(12) United States Patent
Oroskar et al.

(10) Patent No.: US 10,189,762 B1
(45) Date of Patent: Jan. 29, 2019

(54) PROCESS FOR PURIFICATION AND SEPARATION OF CANNABINOIDS, FROM DRIED HEMP AND CANNABIS LEAVES

(71) Applicant: Orochem Technologies, Inc., Naperville, IL (US)

(72) Inventors: Anil Rajaram Oroskar, Oak Brook, IL (US); David W. House, Arlington Heights, IL (US); Praneeth Dayanthe Edirisinghe, Chicago, IL (US); Asha Anil Oroskar, Oak Brook, IL (US); Faridedin Adel, Arlington Heights, IL (US); Xinjie Chen, Naperville, IL (US); Gautham Anil Oroskar, Oak Brook, IL (US)

(73) Assignee: Orochem Technologies, Inc., Naperville, IL (US)

( * ) Notice: Subject to any disclaimer, the term of this patent is extended or adjusted under 35 U.S.C. 154(b) by 0 days.

(21) Appl. No.: 15/644,112

(22) Filed: Jul. 7, 2017

(51) Int. Cl.
| | |
|---|---|
| *C07C 37/82* | (2006.01) |
| *C07C 37/84* | (2006.01) |
| *B01D 15/00* | (2006.01) |
| *C07C 37/68* | (2006.01) |
| *B01D 15/18* | (2006.01) |

(52) U.S. Cl.
CPC ........ *C07C 37/685* (2013.01); *B01D 15/1821* (2013.01); *C07C 37/82* (2013.01); *C07C 37/84* (2013.01)

(58) Field of Classification Search
CPC ....... C07C 37/685; C07C 37/82; C07C 37/84; B01D 15/1821
See application file for complete search history.

(56) References Cited

U.S. PATENT DOCUMENTS

| 2,985,589 | A | 5/1961 | Broughton |
| 9,034,395 | B2 | 5/2015 | Whittle |
| 2004/0033280 | A1 | 2/2004 | Whittle |
| 2005/0266108 | A1 | 12/2005 | Flockhart et al. |
| 2006/0167283 | A1 | 7/2006 | Flockhart |
| 2015/0126596 | A1 | 5/2015 | Gutman et al. |

FOREIGN PATENT DOCUMENTS

| WO | WO 2004/026802 A1 | 4/2004 |
| WO | WO 2016/187679 A1 | 12/2016 |
| WO | WO 2017/194173 A1 | 11/2017 |

OTHER PUBLICATIONS

Brett Konen, "Why Ethanol Works So Well for Cannabis Extraction," Capna Labs, https://www.leafly.com/news/industry/ethanol-cannabis-extraction (Aug. 31, 2016).
HPLC-015 Application News—"Potency Testing in Cannabis Extracts Using a High Resolution Method with Cannabis Analyzer for Potency," Shimadzu Corporation (Feb. 2017).
HPLC-016 Application News—"Potency Testing in Cannabis Extracts Using a High Sensitivity Method with Cannabis Analyzer for Potency," Shimadzu Corporation (Feb. 2017).
HPLC-017 Application News—"Potency Testing in Cannabis Extracts Using a High Throughput Method with Cannabis Analyzer for Potency," Shimadzu Corporation (Feb. 2017).
Meyer et al., "Development of a rapid method for the sequential extraction and subsequent quantification of fatty acids and sugars from avocado mesocarp tissue," *J Agric Food Chem.*, Aug. 27, 2008; 56(16):7439-45. doi: 10.1021/jf8011322. Epub Aug. 5, 2008.
"Pros and Cons of Hemp Oil Extraction Techniques," Elixinol LLC, https://elixinolcbd.com/blogs/buyers-guide/16641671-pros-and-cons-of-hemp-oil-extraction-techniques (Mar. 12, 2015).
European Patent Office, International Search Report and the Written Opinion in International Application No. PCT/US2018/041096 (Oct. 31, 2018).

*Primary Examiner* — Sikarl A Witherspoon
(74) *Attorney, Agent, or Firm* — Leydig, Voit & Mayer, Ltd.

(57) ABSTRACT

Disclosed is a method for purification and separation of cannabinoids, specifically cannabidiol and tetrahydrocannabinol, from the dried hemp and *cannabis* leaves using a combination of a sequence of purification steps including: filtration, decolorization, activation or decarboxylation, dewaxing, a continuous simulated moving bed process, polishing, and crystallization to separate cannabinoids from tetrahydrocannabinol and to provide phytocannabinoid rich oil and cannabidiol isolate. The cannabinoid products can be used in various pharmaceutical and nutraceutical applications.

12 Claims, 8 Drawing Sheets

PROCESS FOR PURIFICATION AND SEPARATION OF CANNABINOIDS, FROM DRIED HEMP AND CANNABIS LEAVES

FIELD OF THE INVENTION

The invention relates to a method for purification and separation of cannabinoids from dried hemp and *cannabis* leaves and continuous purification of cannabinoids. More particularly, the method relates to a process for the continuous purification of cannabinoids extracted from the dried hemp and *cannabis* leaves using simulated moving bed chromatography. Most particularly, the method relates to a novel continuous process for the purification of cannabinoids, specifically cannabidiol and tetrahydrocannabinol using a sequence of purification steps and a continuous simulated moving bed process and downstream recovery steps to separate cannabinoids from tetrahydrocannabinol and to provide phytocannabinoid rich oil and cannabidiol isolate products. The products can be used in various pharmaceutical and nutraceutical applications.

BACKGROUND

The legalization of medicinal *Cannabis* is occurring across the United States and in many other countries. As a result, the global demand for cannabinoids is increasing. In addition, a number of recent medical studies report health benefits of many cannabinoids. *Cannabis* contains over 85 cannabinoids, most of them have been found to have therapeutically beneficial properties. The most widely known cannabinoids found in *cannabis* known to have the most therapeutic properties are cannabidiol (CBD) and tetrahydrocannabinol (THC). A number of other cannabinoids, such as cannabigerol (CBG) and cannabinol (CBN), also have been shown to exhibit health benefits.

Cannabinoids are general known as being psychoactive; however, the psychoactive properties of cannabinoid products depend on the amount of tetrahydrocannabinol (THC) in the products. Accordingly, there is demand for a cannabinoid products that are essentially free of tetrahydrocannabinol (THC), or do not contain tetrahydrocannabinol (THC).

Recently, a number of medical applications for cannabidiol (CBD) relate to treatment of conditions that effect children. Because physicians and parents do not want their children consuming a psychoactive product, there is growing demand for cannabidiol (CBD) without tetrahydrocannabinol (THC). Associated with this demand for a tetrahydrocannabinol (THC) free product, there is a demand for botanically derived and extracted products, rather than synthetically derived products.

The term hemp and *cannabis* refers to the genus *Cannabis*, which contains three species *Cannabis sativa, Cannabis indica*, and *Cannabis ruderalis*. All three species are of the family Cannabaceae, which also includes the genus *Humulus*, or hops. *Cannabis* is a flowering plant that is indigenous to central Asia and India. Humans have been cultivating and using *cannabis* for thousands of years, going back to the ancient Romans, Greeks, and the Islamic empires of the Middle East and Africa.

There are at least 113 different cannabinoids present in the *cannabis* plant. All of the classes of cannabinoids are derived from a common precursor compound, cannabigerol (CBG). The *cannabis* plant also contains a variety of terpenoids. Most such compounds are lipophilic and phenolic.

Below are the structures of many common cannabinoids:

Cannabidiol (CBD)

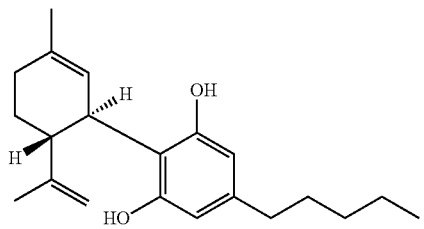 [SMILES: C=C(C)[C@@H]1CCC(C)=C[C@H]1c1c(O)cc(CCCCC)cc1O]

Tetrahydrocannabinol (THC)

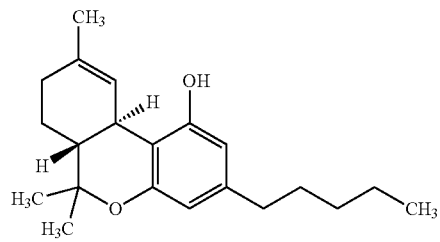 [SMILES: CCCCCc1cc(O)c2c(c1)OC(C)(C)[C@@H]1CCC(C)=C[C@@H]21]

Cannabigerol (CBG)

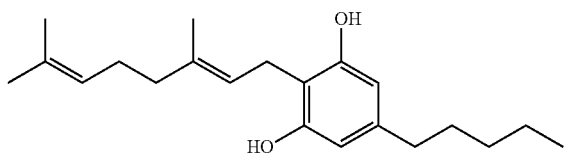 [SMILES: CCCCCc1cc(O)c(C/C=C(\C)CCC=C(C)C)c(O)c1]

Cannabinol (CBN)

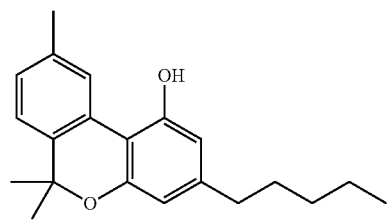 [SMILES: CCCCCc1cc(O)c2c(c1)OC(C)(C)c1ccc(C)cc1-2]

Cannabinoids can be extracted from dried hemp and *cannabis* leaves of the three species *Cannabis sativa, Cannabis indica*, and *Cannabis ruderalis* using a hydrocarbon solvent such as butane, a supercritical solvent such as carbon dioxide, or ethanol. Butane extraction and supercritical $CO_2$ extraction, have accounted for the majority of production of cannabinoid concentrates currently available on the market. A third extraction method, based on ethanol has been gaining market share as a solvent of choice for manufacturing high-quality *cannabis* extracts.

Butane is a gas at standard conditions, and requires the extraction to be carried out at above atmospheric pressure. Following the extraction, butane is relatively easy to purge from the resulting extract because of its lower boiling point. However, the largest drawback to using butane for the extraction of cannabinoids is safety. Butane is highly combustible, and its use has resulted in a number of explosions in small extractors. Furthermore, there is concern that if the butane is not pure, undesirable and potentially toxic hydrocarbons can end up in the extract product.

Liquid carbon dioxide can be employed to extract cannabidiol (CBD) and other cannabinoids from the *cannabis* plant. The extraction is performed using liquid carbon dioxide (CO2) in its super-critical range, typically at extraction temperatures above 31° C. and pressures above 74 bar. According to the super critical extraction process, the solid matrix (leaves) to be extracted is loaded into a pressurized chamber, into which the liquid carbon dioxide is then pumped. The desired extractable component, cannabidiol (CBD), will dissolve in the carbon dioxide to form a solution. The resulting solution is pumped into a settling chamber, which is at a lower pressure. At the reduced pressure of the settling chamber, the dissolved solid precipitates. Solubility of the cannabidiol in the supercritical fluid is directly related to pressure. Once the solute has precipitated out of the solution the carbon dioxide will be pumped out and will be recom pressed for further use in extraction. Supercritical $CO_2$ extraction is effective because: $CO_2$ is inert and non-toxic, and, 2) $CO_2$ is non polar. However, $CO_2$ will also extract many plant waxes, lipids, and other non-polar and undesired components. Because supercritical $CO_2$ extraction must be run at high pressure, there is additional cost and safety problems with the extraction equipment and apparatus itself.

Even though ethanol is safer than butane and more effective than supercritical CO2, a standard ethanol extraction introduces other difficulties. The polar nature of ethanol allows ethanol to readily mix with water and dissolve water soluble molecules during the extraction process. This results in a greater amount of impurities being introduced into the extract. For example, chlorophyll will be co-extracted with ethanol and the resulting extract will have a dark color and an unpleasant taste. As a result, using ethanol extraction requires a large number of downstream purification steps, including expensive column chromatography, in order to meet pharmaceutical purity specifications.

US patent publication No. US20060167283 A1 discloses methods to purify and isolate cannabidiol (CBD) from dried plant material which include (a) decarboxylating the leaves (b) extracting cannabinoids using supercritical carbon dioxide (c) precipitation using $C_1$-$C_{12}$ alcohol (d) filtration (e) redissolving the cannabidiol enriched extract into pentane (f) removal of insoluble material and (g) evaporation of solvent producing crystals.

U.S. Pat. No. 9,034,395 discloses a method for preparing extracts of natural products such as plant material, and for preparing purified extracts from crude extracts of natural products, by extraction with hot gas. The cannabinoids are volatilized at a high temperature along with a heated gas. The cannabinoids are volatilized in one or more stages at increasing temperatures, and the volatilized components are condensed and collected at one or both stages.

Over forty years ago, a new process was developed specifically for large scale industrial purifications. U.S. Pat. No. 2,985,589 disclosed a chromatography system involving a separation tower divided into a number of individual separation beds. These beds are connected in series, and the outlet at the bottom most bed is connected to a pump that returned flow in a continuous loop to the upper most bed. The inlet apparatus for each bed has a port connected to a downward flowing conduit. The conduits terminate in fittings attached to a rotary valve designed to control both ingress and egress of liquids into or from the inlets to each individual bed. The system is called Simulated Moving Bed (SMB) chromatography because the beds appear to be moving in a direction countercurrent to the direction of flow. There are hundreds of adsorbents which have been used for simulated moving bed systems, some of which include resins, zeolites, alumina, and silica.

Simulated Moving Bed (SMB) technology represents a variation on the principles of high performance liquid chromatography. SMB can be used to separate particles and/or chemical compounds that would be difficult or impossible to separate by any other means. Furthermore, SMB technology represents a continuous process which provides a significant economic and efficiency advantages in manufacturing operations compared to batch typical batch separation methods including crystallization and stepwise chromatographic separations.

Conventional methods for the purification of cannabinoids are associated a large number of downstream purification steps, including expensive column chromatography, in order to meet high purity specifications. Methods are sought to purify and recover a cannabidiol (CBD) rich oil which contains essentially no THC. To satisfy the growing demand for the cannabidiol (CBD) oil being essentially free of tetrahydrocannabinol (THC), there is a need for an efficient extraction process that can be carried out on a commercial scale to produce high purity cannabidiol (CBD) products. The potential for even small amounts of THC remaining in the purified CBD oil product can be is undesirable.

SUMMARY

The process of the present invention relates to the purification and separation cannabinoids from dried hemp and *cannabis* leaves and continuous purification of cannabinoids. in a process which uses novel a chromatographic scheme. More specifically, Applicant has developed a sequence of purification steps and a novel simulated moving bed separation (SMB) process to bring about the enrichment and purification of Cannabidiol (CBD) which is essentially pure and is essentially free of Tetrahydrocannabinol (THC). Furthermore, the process provides a highly pure CBD product without using any potentially toxic organic solvent. The feed to the SMB unit incorporates a series of steps which essentially eliminate the presence of THC. The simulated moving bed system employed is a combination of a reverse phase stationary phase adsorbent and a polar mobile phase comprising ethanol and water in reverse phase simulated moving bed separation zone to provide an enriched raffinate stream comprising cannabinoids, primarily CBD, which is essentially free of tetrahydrocannabinol (THC). A cannabidiol product having a total cannabidiol (CBD) purity greater than 95 wt percent (e.g., 96, 97, 98, 99, 99.9 wt-%) following evaporation or drying can be obtained.

In one embodiment, the invention is process for the purification of cannabidiol (CBD) in a crude *cannabis* extract stream to provide at least one high purity cannabidiol product selected from the group consisting of a high purity cannabinoid oil stream, a phytocannabinoid rich oil, a solid CBD aggregate and mixtures thereof being essentially free of tetrahydrocannabinol, said process comprising:

a) passing the crude *cannabis* extract stream comprising debris and small particles, cannabidiol, tetrahydrocannabinol, cannabidiolic acid, tetrahydrocannabinolic acid, other cannabinols, chlorophylls, color bodies, sugars and carbohydrates, lipids, plant waxes, impurities, and ethanol to a first filtration zone comprising a series of successive filters of decreasing pore size, starting at a pore size of 100 microns and reducing to about 10 microns in 3 or more stages to remove debris and small particles in a progressive filtration step to provide a filtered crude cannabinoid stream;

b) passing the filtered crude cannabinoid stream comprising cannabidiol, tetrahydrocannabinol, cannabidiolic acid, tetrahydrocannabinolic acid, other cannabinols, chlorophylls, color bodies, sugars and carbohydrates, lipids, plant waxes, impurities, and ethanol to a decolorization zone comprising a 10 μm filter and a decolorization chromatographic column containing a modified activated carbon adsorbent which was heat treated to provide a highly hydrophobic adsorbent which is essentially free of hydroxyl groups, has an average particle diameter of between 177 and 250 microns, and an iodine number of above 900 mg/g and operated at a decolorization pressure of 2.72 atm to about 4.08 atm (40-60 psig) and a decolorization temperature ranging from 20-25° C. to remove at least a portion of color bodies and essentially all of the chlorophyll to provide a decolorized extract stream;

c) passing the decolorized extract stream to a first evaporation zone operated at a first vacuum pressure of −0.60 to about −0.74 atm (−18 to −22 in Hg) and a temperature of about 90 to about 110° C. to remove at least a portion of the ethanol to provide an evaporated extract stream which is essentially free of ethanol;

d) passing the evaporated extract stream comprising cannabidiol (CBD), cannabidiolic acid (CBDA), tetrahydrocannabinolic acid (THCA), tetrahydrocannabinol (THC), sugars and carbohydrates, lipids, plant waxes, impurities and other cannabinoids to an activation zone and therein subjected to a carboxylation reaction at a decarboxylation temperature of about 90 to about 120° C. and a decarboxylation pressure of about −0.6 atm to 0.74 atm for a decarboxylation reaction time of about 5 to about 8 hours, or sufficient time for the decarboxylation reaction to occur and proceed to completion, said decarboxylation reaction time being sufficient to fully decarboxylate essentially all of the cannabidiolic acid (CBDA) and tetrahydrocannabinolic acid (THCA) to provide a decarboxylated cannabinoid oil comprising cannabidiol (CBD), tetrahydrocannabinol (THC), lipids, plant waxes, and other cannabinoids, and being essentially free of cannabidiolic acid (CBDA) and tetrahydrocannabinolic acid (THCA), and water washing the decarboxylated cannabinoid oil to remove at least a portion of the impurities to provide a washed decarboxylated cannabinoid oil;

e) admixing the washed decarboxylated cannabinoid oil with a dewaxing solvent having a dewaxing solvent volume ratio of 80 volume units of ethanol to 20 volume units water to provide a dewaxing feed stream and passing the dewaxing feed stream to a dewaxing zone containing a dewaxing column at a dewaxing column pressure of about 2.72 atm to about 4.08 atm (40-60 psi) and room temperature (20-25° C.), said dewaxing column containing a hydrophobic activated carbon adsorbent which is essentially free of hydroxyl groups, and having an average particle diameter of between 177 and 250 microns, and an iodine number of above 900 mg/g to remove at least a portion of the lipids and plant waxes and to provide a dewaxed cannabinoid oil stream comprising cannabidiol (CBD), tetrahydrocannabinol (THC), sugars and carbohydrates, color bodies, and other cannabinoids;

f) passing the dewaxed cannabinoid oil stream and a mobile phase desorbent stream consisting of a mixture of food grade ethanol and water to a reversed phase simulated moving bed zone comprising a plurality of adsorbent beds containing a modified hydrophobic adsorbent comprising a styrene-divinylbenzene (DVB) resin having 4 to 8 percent crosslinking or a poly(methyl methacrylate) (PMMA) resin, said modified hydrophobic adsorbent having an average particle diameter of between 25 and 300 microns, an average bulk density (gm/mL) of from 0.4 to 0.6, a surface area (m2/g) of from 450 to 550, and a pore volume of from 0.70-0.90 (mL/g) to provide a primary raffinate stream comprising cannabidiol (CBD), mobile phase desorbent, sugars and carbohydrates, color bodies, and other cannabinoids and being essentially free of tetrahydrocannabinol (THC), an extract stream comprising mobile phase desorbent, cannabidiol (CBD), and tetrahydrocannabinol (THC), and a secondary raffinate stream comprising mobile phase desorbent, cannabidiol (CBD) which is admixed with the mobile phase desorbent and returned to the reversed phase simulated moving bed zone;

g) passing the primary raffinate to a second evaporation zone to remove mobile phase desorbent to provide a second recovered solvent stream comprising the mobile phase desorbent and to provide the high purity cannabinoid oil stream having an average cannabidiol purity of greater than 80 wt % and being essentially free of tetrahydrocannabinol (THC);

h) passing at least a portion of the high purity cannabinoid oil stream to a polishing zone and therein admixing the high purity cannabinoid oil stream with a non-polar solvent stream comprising hexane and therein allowing the admixture to settle to form a precipitate comprising sugars and carbohydrates and a supernatant non-polar solution comprising cannabidiol (CBD), color bodies, and other cannabinoids;

i) passing a portion of the supernatant non-polar solution to a second filtration zone to remove the precipitate and to provide a filtered supernatant non-polar solution;

j) passing the filtered supernatant non-polar solution to a third evaporation zone to remove at least a portion of the non-polar solvent to provide an evaporated cannabinoid oil stream and a recovered non-polar solvent stream, and returning at least a portion of the recovered non-polar solvent stream to the polishing zone to be admixed with the non-polar solvent;

k) passing the evaporated cannabinoid oil stream to a wash zone and alternately washing the evaporated cannabinoid oil stream first with an ethanol wash stream comprising pure ethanol in a washing ratio of 1:3 liters of ethanol to kilograms of evaporated cannabinoid oil, and second with a fourth water wash stream in a water wash ratio of 1:3 liters of water to kilograms of evaporated cannabinoid oil, and wherein following each step, washed cannabinoid oil is evaporated to dryness to provide a phytocannabinoid rich oil which is essentially free of tetrahydrocannabinol (THC) and comprising greater than 80 wt-% cannabinoid (CBD);

l) passing a portion of the supernatant non-polar solution to a isolate chromatography zone comprising a first isolate chromatography column and a second isolate chromatography column being in serial fluid communication and wherein the first isolate chromatography column contains a modified hydrophilic adsorbent comprising a spherical polar silica adsorbent having a high level of silenol groups, an average particle diameter of between 60 and 200 microns, a surface area of between 450 to 550 m2/g a pore volume of between 0.7 and 0.85 mL/g and a pore size of between 0.005 and 0.0075 microns, wherein the second isolate chromatography column contains an activated alumina adsorbent having an average particle diameter of between 50 to 200 microns, an average bulk density of 0.85 g/ml, a surface area of between 140 and 170 m2/g, and an average pore diameter of greater than 0.006 microns to provide an isolate elute stream comprising cannabidiol (CBD), non-polar solvent and other cannabinoids;

m) passing the isolate elute stream to a crystallization zone, wherein the isolate elute stream is subjected to a freezer temperature of equal to or less than about −20° C. for a freezer period of about 24 to about 72 hours to permit primary high purity cannabidiol crystals, containing from about 96 to about 98 wt-% cannabidiol to form, harvesting the primary high purity cannabidiol (CBD) crystals and admixing the primary high purity cannabidiol crystals with hexane to provide the crystal isolate solution comprising 20-30% by weight cannabidiol CBD oils, and retaining the crystal isolate solution at room temperature for a period of 24-72 hours to permit secondary high purity CBD crystals to form and harvesting the secondary high purity CBD crystals;

n) passing the secondary high purity CBD crystals to a rotary evaporation zone wherein the secondary high purity crystals are heated until molten to evaporate any residual non-polar and washed with a third water wash stream at least three times in the rotary evaporation, wherein at the completion of each wash step the secondary high purity crystals are dried to complete dryness to provide a solid CBD aggregate which is essentially free of tetrahydrocannabinol (THC) and has a cannabidiol purity of greater than 99 wt-%; and, o) withdrawing at least one high purity cannabidiol product being essentially free of tetrahydrocannabinol (THC) a stream selected from the group consisting of the high purity cannabinoid oil stream, the phytocannabinoid rich oil, the solid CBD aggregate and mixtures thereof.

The purified product of the present invention comprises Cannabidiol (CBD) concentration greater than about 98% (w/w) on an anhydrous basis.

BRIEF DESCRIPTION OF THE DRAWINGS

The accompanying drawings are included to provide a further understanding of the invention. The drawings illustrate embodiments of the invention and together with the description serve to explain the principles of the embodiments of the invention.

DETAILED DESCRIPTION OF THE INVENTION

Figure 1:
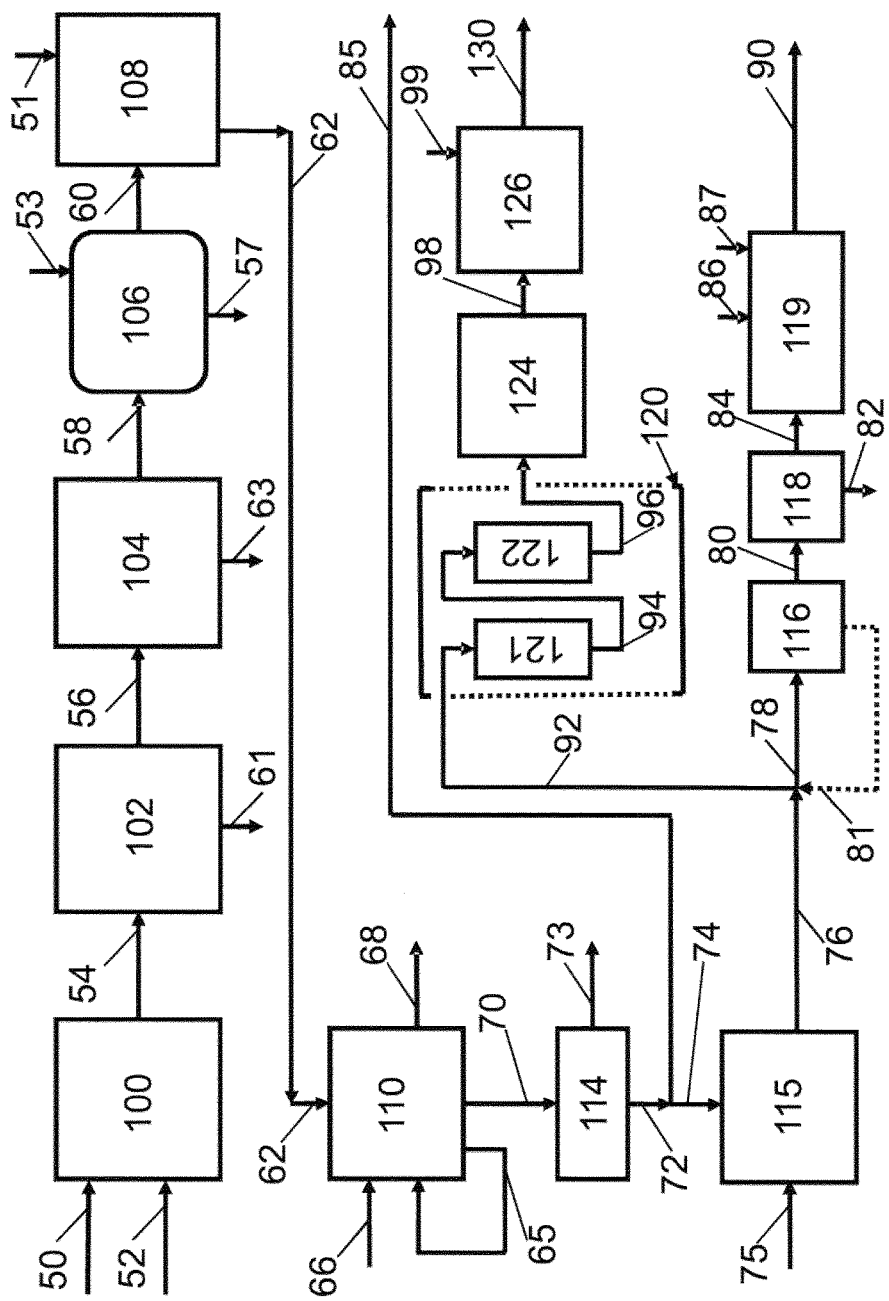
FIG. 1 is a schematic process flow diagram illustrating a configuration of the continuous overall process for recovery and purification of cannabidiol.

Industrial hemp, or agricultural hemp, and medical marijuana both come from the *Cannabis Sativa* L. plant. Industrial hemp, which is often referred to as "hemp stalk," grows differently than THC-containing *cannabis*, and looks similar to bamboo. Cannabinoids are a family of naturally occurring $C_{21}$ terpenophenolic compounds uniquely produced in *cannabis*. Marijuana usually refers to a mixture of leaves and flowering heads of the pistillate plant of *Cannabis sativa* from which tetrahydrocannabinols (THCs) are isolated. THCs contain two main isomeric forms, depending on the position of the double bond. The position of the double bond and the stereochemistry of these THCs have been confirmed by nuclear magnetic resonance and X-ray structure.

Extracting active ingredients from *cannabis* routinely extracts a number of impurities which are difficult to remove from the finished product; and, therefore a large number of purification steps, including expensive column chromatography, are required to isolate components.

The following are typical abbreviations for commonly found cannabinoids in the extract of hemp leaves:

| | |
|---|---|
| THC | Tetrahydrocannabinol, |
| THCV | Tetrahydrocannabivarin |
| CBG | Cannabigerol |
| CBD | Cannabidiol |
| CBN | Cannabinol |
| THCA | Tetrahydrocannabinolic Acid |
| CBDA | Cannabidiolic Acid |
| CBDV | Cannabidivarin |

As used herein, the term "reversed-phase chromatography" employs a polar (aqueous) mobile phase. As a result, hydrophobic molecules in the polar mobile phase tend to adsorb to the hydrophobic stationary phase, and hydrophilic molecules in the mobile phase will pass through the column and are eluted first.

As used herein, the term "solid concentration" refers to the mass of solids per volume of liquid in a given stream and is expressed as grams/Liter. The mass of the solids content in a stream is determined by subjecting a fixed volume of the sample, typically 1 ml, to an effective amount of heat, up to 80° C., at atmospheric pressure for a time sufficient to fully evaporate the sample to dryness, typically 1-2 hours.

Applicant discovered a sequence of process operations for purifying the crude extract of the *Cannabis* plant which includes a filtration zone, a decolorization zone, an activation zone, a dewaxing zone, a simulated moving bed zone, a second filtration zone, a purification zone, a concentration zone, a crystallization zone. Applicant's scheme provides a scheme wherein no toxic solvents are required to provide a high purity Cannabidiol (CBD) product which is essentially free of tetrahydrocannabinol.

The SMB system of the current invention was arranged for maximum selectivity. The simulated moving bed operation is achieved by use of a plurality of adsorbent beds connected in series or portions in series or parallel and a complex valve system, whereby the complex valve system facilitates switching at regular intervals the feed entry in one direction, the mobile phase desorbent entry in the opposite direction, while changing the extract and raffinate takeoff positions as well. The SMB system is a continuous process. Feed and mobile phase desorbent enter and extract and raffinate streams are withdrawn continuously at substantially constant compositions. The overall operation is equivalent in performance to an operation wherein the fluid and solid are contacted in a continuous countercurrent manner, without the actual movement of the solid, or stationary phase adsorbent.

The SMB system may be operated such that the adsorbent beds are operated individually or in parallel using a single rotary valve and associated control system. A column may comprise one or more beds containing chromatographic media. Those feed tanks, filters, piping connecting flow between columns and/or beds where so connected, pumps, valving, pressure regulators, metering equipment, flow control and microprocessor equipment utilized in the embodiment are well known in construction and function to those of ordinary skill in the art.

Stationary Phase

The stationary phase adsorbents may be disposed in a single adsorbent bed or may be disposed in within a single column or series of single columns containing multiple adsorbent bed zones. The instant invention employs four separate stationary phase adsorbents in carrying out the overall process of the invention. Although reverse phase adsorbents such as C18 have been employed in analysis of cannabinoids, it was discovered that the use of C18 type of reverse phase adsorbents in simulated moving bed systems was subject to inefficiencies and inconsistent retention of terpenes resulting in product quality inconsistencies.

OR1 is a modified activated carbon adsorbent which was heat treated to provide a highly hydrophobic adsorbent which is essentially free of hydroxyl groups, and has an average particle diameter of between 177 and 250 microns, and an iodine number (a measure of the micropore content of the activated carbon) of above 900 mg/g.

OR2 is modified hydrophobic adsorbent comprising a styrene-divinylbenzene (DVB) resin having 4 to 8 percent crosslinking or a poly(methyl methacrylate) (PMMA) resin. The OR2 hydrophobic adsorbent has an average particle diameter of between 25 and 300 microns, an average bulk density (gm/mL) of from 0.4 to 0.6, a surface area (m2/g) of from 450 to 550, and a pore volume of from 0.70-0.90 (mL/g).

OR3 is a modified hydrophilic adsorbent comprising a spherical polar silica adsorbent having a high level of silenol (Si—O—H) groups, having an average particle diameter of between 60 and 200 microns, having a surface area of between 450 and 550 $m^2/g$, having a pore volume of between 0.7 and 0.85 mL/g, and having a pore size of between 50 to 75 Angstroms (0.005-0.0075 microns).

OR4 is an activated alumina adsorbent having an average particle diameter of between 50 and 200 microns, an average bulk density of 0.85 g/ml, a surface area of between 140-170 $m^2/g$, and an average pore diameter of greater than 60 Angstroms (0.006 microns).

Mobile Phase Desorbent

The mobile phase desorbent of the present invention for use in the SMB zone for all adsorbents is a mixture of food grade ethanol and water, preferably deionized water. The mobile phase desorbent employs a ratio of ethanol to water of from about 70 to 90 parts ethanol (Food grade ethanol—200 Proof) to about 10 to 30 parts water. More preferably, the ratio of ethanol to water in the mobile phase is 80 parts ethanol to 20 parts water.

Feed Preparation

In the present invention, following harvesting and processing, the grinded and dried *cannabis* leaves are extracted with an appropriate GRAS solvent, preferably ethanol, or mixtures of ethanol and water. A number of different parameters can influence the overall yield, quality and/or purity of the desired final product. These parameters include, but are not limited to, the identity of the chosen GRAS solvent; the temperature and time at which the chosen natural solvent is used; the ratio of raw material to solvent (raw material: solvent (v/v)) that is employed; the number of successive extractions performed; the chosen method of purification of the desired products and the conditions related thereto. The skilled person will understand that these parameters are not necessarily mutually exclusive, and that a particular choice relating to one parameter may or may not affect the choice of other parameters. For example, the identity of the chosen natural solvent, and the temperature thereof, can affect the optimal ratio of raw material to solvent that is required to obtain the desired results. Following the extraction of the cannabinoids from the *cannabis* leaves, a crude extract stream comprising crude cannabinoids and impurities is provided in the extraction zone. The crude cannabinoid stream is filtered to remove debris and small particles in a progressive filtration step to provide a filtered crude cannabinoid stream.

Preferably, the crude cannabinoids are admixed with ethanol to provide a filtered crude cannabinoid stream which comprises from about 3.4 wt-% to about 4.0 wt-% total crude cannabinoids in the mixture. More preferably, the filtered crude cannabinoid stream comprises from about 3.4 wt-% to about 3.7 wt-% total cannabinoids in the mixture. The concentration of solids in the filtered crude cannabinoid stream varies from about 60 to about 80 g/l and is preferably about 75 g/l.

DETAILED DESCRIPTION OF THE DRAWINGS

According to one embodiment of the invention and with reference to FIG. 1, a process is disclosed for the separation and purification of cannabidiol (CBD) from dried *cannabis* leaves from the *Cannabis sativa*, *Cannabis indica*, or *Cannabis ruderalis* plant are passed in line 50 to an extraction/filtration zone 100 and therein admixed with an effective amount of ethanol in line 52 and agitated by conventional means to provide a crude cannabinoid extract stream. Preferably, the crude cannabinoids are admixed with ethanol to provide a filtered crude cannabinoid stream which comprises from about 3.4 wt-% to about 4.0 wt-% total crude cannabinoids in the mixture. More preferably, the filtered crude cannabinoid stream comprises from about 3.4 wt-% to about 3.7 wt-% total cannabinoids in the mixture. The concentration of solids in the filtered crude cannabinoid stream varies from about 60 to about 80 g/l and is preferably about 75 g/l. The crude cannabinoid extract stream is then filtered in the first filtration zone of the extraction/filtration zone 100, in a series of successive filters of decreasing pore size, starting at a pore size of 100 microns and reducing to about 10 microns in 3 or more stages. Preferably, the successive filters comprise a 100 micron, a 20 micron, and a 10 micron filter. The 100 micron pore size filter comprises a bag filter made of felt for high capacity flow and capturing solids. The 20 and 10 micron pore size filters consist of cartridges comprising polyethylene and are pleated for providing higher surface area. The cartridges had O-rings on a fitting at the end for seating and are adapted to be disposed inside a cylindrical, stainless steel housing. The filtered liquid leaf extract stream, or filtered crude extract stream comprises cannabidiol (CBD), cannabidiolic acid (CBDA), tetrahydrocannabinol (THC), tetrahydrocannabinolic acid (THCA), other cannabinols, color bodies, impurities and ethanol. The filtered crude extract stream is green in color due to the presence of the color bodies and chlorophyll, is essentially free of particles, and is comprised of approximately 20-40 g/L of cannabidiol (CBD) and cannabidiolic acid (CBDA). The filtered crude extract stream is withdrawn from the extract/filtration zone 100 in line 54. The filtered crude extract stream in line 54 is passed to a decolorization zone 102 to remove at least a portion of color bodies and provide a decolorized crude extract stream in line 56. In the decolorization zone 102, the filtered crude extract stream was passed through a 10 µm filter to the top of a decolorization chromatographic column. The column was operated at a decolorization pressure of 2.72 atm to about 4.08 atm (40-60 psig) and a decolorization temperature ranging from 20-25° C. The decolorization chromatographic column was packed with adsorbent OR1, a modified activated carbon adsorbent which was heat treated to provide a highly hydrophobic adsorbent which is essentially free of hydroxyl groups, has an average particle diameter of between 177 and 250 microns, and an iodine number of above 900 mg/g. At least a portion of the color bodies are selectively retained on the decolorization chromatographic column adsorbent, shown as line 61; and, the recovered elute is withdrawn as a decolorized extract stream in line 56. Essentially all chlorophylls were removed from the filtered crude extract stream in line 61 following a decolorization wash, although some color bodies remain resulting in an amber color of the decolorized extract stream. The solids concentration in the decolorized extract stream is about 40-45% cannabidiol (CBD) and cannabidiolic acid (CBDA) and the concentration of total solids in the decolorized extract stream is approximately 20-35 g/L. The solids concentration was determined following evaporation of the ethanol from the decolorized extract stream to dryness. The decolorized extract stream in line 56 was passed to a first evaporation zone 104 to remove the ethanol solvent from the decolorized extract stream in line 56 to provide an evaporated extract stream in line 58 and a first recovered ethanol stream in line 63. In the first evaporation zone 104 the decolorized extract stream in line 56 was subjected to vacuum distillation, to remove essentially all of the solvent from the decolorized extract stream in line 56. The vacuum distillation was operated at a vacuum pressure of about −0.60 to about −0.74 atm (−18 to −22 in Hg) and a temperature of about 90 to about 110° C. At least a portion of ethanol solvent recovered from the vacuum distillation unit as a first recovered ethanol stream in line 63 was reused, i.e., recycled, as solvent for the extraction/filtration zone 100. Following removal of the ethanol solvent in line 63, the remaining cannabinoid oil comprising cannabidiol (CBD), cannabidiolic acid (CBDA), tetrahydrocannabinolic acid (THCA), tetrahydrocannabinol (THC), lipids and plant waxes, impurities and other cannabinols was passed to an activation zone 106 and therein subjected to an activation step. The activation zone 106 could be a physically separate zone or the remaining cannabinoid oil in line 58 can be retained in the vacuum distillation vessel for heating. The activation step comprises a decarboxylation reaction wherein the remaining cannabinoid oil in line 58 was subjected to a decarboxylation temperature of about 90 to about 120° C. and a decarboxylation pressure of about −0.6 atm to 0.74 atm for a decarboxylation reaction time of about 5 to about 8 hours, or sufficient time for the decarboxylation reaction to occur and proceed to completion. The decarboxylation reaction time was sufficient to fully decarboxylate essentially all of the acidic components to provide a decarboxylated cannabinoid oil comprising cannabidiol (CBD), tetrahydrocannabinol (THC), lipids and plant waxes, and other cannabinoids, and being essentially free of cannabidiolic acid (CBDA) and tetrahydrocannabinolic acid (THCA). During the course of the decarboxylation reaction, it was surprisingly discovered that at least a portion of impurities in the remaining cannabinoid oil in line 58 were aggregated into a sludge like material which floated on top of the decarboxylated cannabinoid oil. Thus, following the decarboxylation reaction, a first water wash step was performed to remove the aggregated impurities, by subjecting the decarboxylated cannabinoid oil to the water wash step, wherein a first water wash stream in line 53 is introduced to solubilize the impurities and to remove the aggregated impurities in line 57 from the decarboxylated cannabinoid oil stream in line 60. At the conclusion of the decarboxylation and water wash steps, the decarboxylated cannabinoid oil stream in line 60 is passed to a dewaxing zone 108. In the dewaxing zone, at least a portion of lipids and plant waxes are removed from the decarboxylated cannabinoid oil stream. In the dewaxing zone 108, the decarboxylated cannabinoid oil stream in line 60 is admixed with a solution in line 51 containing ethanol and water sufficient to provide a dewaxing solvent volume ratio of 80/20 solvent volume to volume of decarboxylated cannabinoid oil (800 L of ethanol and 200 L of water to make 1000 L of the mixture) and to provide a dewaxing feed stream. The dewaxing feed stream comprises about 40-45 g/L concentration of total solids (on a dry basis). It was discovered that it was critical that the concentration of solids in the dewaxing feed stream not exceed a dewaxing feed solids concentration 50 g/L on a dry basis. The dewaxing feed stream was passed to the top of a dewaxing column at a dewaxing column pressure of about 2.72 atm to about 4.08 atm (40-60 psi) and room temperature (20-25° C.). The dewaxing column was packed adsorbent OR1, a hydrophobic activated carbon adsorbent which is essentially free of hydroxyl groups, and has an average particle diameter of between 177 and 250 microns, and an iodine number of above 900 mg/g. The effluent from the dewaxing column, or dewaxed cannabinoid oil stream in line 62 comprises cannabidiol (CBD), tetrahydrocannabinol (THC), and other cannabinoids, and has a concentration of total solids in the dewaxed cannabinoid oil stream in line 62 of from 35 to 40 g/L, and comprises about 60 wt-% cannabidiol on a dry basis. The dewaxed cannabinoid oil stream in line 62 is withdrawn from the dewaxing zone 108 and passed via lines 62 to a simulated moving bed (SMB) zone 110 for reverse phase separation. The simulated moving bed zone 110 is further described hereinbelow in connection with FIG. 2. The simulated moving bed zone 110 consists of 8 SMB adsorbent beds, and also comprises a rotary valve, an arrangement of valves and piping, and a valve control system, which for simplicity are not shown. Each of the simulated moving bed (SMB) adsorbent beds contain a simulated moving bed (SMB) stationary phase adsorbent consisting of OR2. OR2 is modified hydrophobic adsorbent comprising a styrene-divinylbenzene (DVB) resin having 4 to 8 percent crosslinking or a poly(methyl methacrylate)

(PMMA) resin. The OR2 hydrophobic adsorbent has an average particle diameter of between 25 and 300 microns, an average bulk density (gm/mL) of from 0.4 to 0.6, a surface area (m2/g) of from 450 to 550, and a pore volume of from 0.70-0.90 (mL/g). In the simulated moving bed zone 110, a mobile phase desorbent stream is introduced via line 66. The simulated moving bed (SMB) zone 110 provides a primary raffinate stream in line 70, an extract stream in line 68, and a secondary raffinate stream in line 65. The secondary raffinate stream in line 65 is returned to the simulated moving bed zone to be admixed with the mobile phase desorbent stream to offset the need for desorbent. The extract stream comprises mobile phase desorbent, cannabidiol (CBD), and tetrahydrocannabinol (THC) and is passed to desorbent recovery. Following the removal of the mobile phase desorbent by vacuum distillation (not shown) the recovered mobile phase desorbent may be recycled to the simulated moving bed zone and the resulting solvent free extract stream is passed to waste disposal. The primary raffinate stream in line 70 comprises cannabidiol (CBD), dewaxing solvent, and is essentially free of tetrahydrocannabinol (THC), and comprises an average primary raffinate solids concentration of 5.0-7.0 g/L and has an average cannabidiol (CBD) purity of 80-87% w/w and an average THC content of 0.0% wt-%. The primary raffinate stream in line 70 is passed to a second evaporation zone 114, operating at a second evaporation temperature of about 80-100° C. and a second evaporation pressure of about −0.53 to −0.67 atm (−16 to −20 in Hg) to separate the primary raffinate stream into a high purity cannabinoid oil stream in line 72 and a second recovered solvent stream on line 73. At least a portion of the high purity cannabinoid oil stream can be withdrawn via lines 72 and 85 as a high purity cannabidiol oil (CBD) product, or the remainder of the high purity cannabinoid oil stream is passed for further purification via lines 72 and 74 to a polishing zone 115. In the polishing zone 115, the high purity cannabinoid oil stream in line 74, which is essentially free of any solvent, was further processed to remove polar impurities. The high purity cannabinoid oil stream in line 72 is passed to a polishing zone 115, wherein the high purity cannabinoid oil stream is admixed with a sufficient amount of a non-polar solvent, such as hexane, introduced in line 75, to provide a polishing zone feed stream having a cannabidiol (CBD) oil concentration of about 10-30 wt-% cannabidiol (CBD) oil. The polishing zone feed stream is agitated and allowed to settle at room temperature for a period of 120 to 720 minutes to allow the polar compounds, such as sugars and carbohydrates, to precipitate from the supernatant non-polar solution, and the supernatant non-polar solution is passed to a second filtration zone 116 via lines 76 and 78 to separate the precipitate the sugars and carbohydrates from the supernatant non-polar solution to provide a filtered supernatant non-polar solution in line 80. The filtered supernatant non-polar solution in line 80 is passed to a third evaporation zone 118 to recover essentially all of the non-polar solvent to provide recovered non-polar solvent, comprising hexane, in line 82 and to provide an evaporated cannabinoid oil stream in line 84. At least a portion of the recovered non-polar solvent in line 82 may be returned to the polishing zone 115 to be admixed with the non-polar solvent to provide makeup non-polar solvent. The evaporated cannabinoid oil stream in line 84 is passed to a wash zone 119, wherein the evaporated cannabinoid oil stream is alternately washed up to at least 3 times, first with an ethanol wash stream comprising 100 wt % ethanol introduced via line 86 in an alcohol wash ratio of 1:3 L of ethanol to Kg of evaporated cannabinoid oil; and second, with a fourth water wash stream in line 87 using a water wash ratio of 1:3 L of water to Kg of cannabinoid oil, and wherein after each wash step, the washed cannabinoid oil is evaporated to dryness. At the conclusion of the last water wash and drying steps, a phytocannabinoid rich oil, essentially free of tetrahydrocannabinol (THC) is withdrawn in line 90. Being essentially free of tetrahydrocannabinol (THC) means that the concentration of tetrahydrocannabinol (THC) in the phytocannabinoid rich oil is less than 0.001 wt-%, or non-detectable (ND).

The phytocannabinoid rich oil composition is described hereinbelow in Tables 1 and 2. Table 1 shows the composition of the cannabinoids in the Phytocannabinoid rich oil, and Table 2 shows the residual solvent analysis. No detectable solvent was present in the phytocannabinoid rich oil product, and the phytocannabinoid rich oil product is free of any THC.

TABLE 1

Cannabinoid profile of Phytocannabinoid rich oil

| Compound | Amount reported % |
| --- | --- |
| THC | 0 |
| THCV | 0 |
| CBG | 0-4% |
| CBD | 70-86% |
| CBN | 0-3% |
| THCA | 0 |
| CBDA | 0 |
| CBDV | 0-1% |
| Other | 30-10% |

TABLE 2

Residual Solvent Analysis of Phytocannabinoid rich oil

| Solvent | Amount Reported |
| --- | --- |
| Ethanol | ND |
| Isopropanol | ND |
| Hexane | ND |
| Ethyl Acetate | ND |
| Heptane | ND |

ND - None Detected

Cannabinoid Isolate Preparation

Alternatively, the supernate hexane solution in line 78 can be further processed to provide a cannabinoid isolate product. Accordingly, the supernate non-polar solution in line 76, or the filtered supernate non-polar solution in lines 81 and 92 is passed to an isolate chromatography zone 120 via line 92. The isolate chromatography zone 120 comprises a first isolate chromatography column 121 and a second isolate chromatography column 122, wherein the first and the second isolate chromatography columns (121, 122) are serially connected and in serial fluid communication. The supernate hexane solution in line 78 or the filtered supernate hexane solution in line 81 is passed to the top of the first isolate chromatography column 121 via line 92 and the effluent from the first isolate chromatography column 121 is withdrawn in line 94 and passed to the top of the second isolate chromatography column 122. The effluent from the second isolate chromatography column 122 is withdrawn via line 96 from the bottom of the isolate chromatography column 122. The first isolate chromatography column 121 can be one or more physical column containing the OR3 adsorbent, and the second isolate chromatography column 122 can be one or more physical column containing the OR4 adsorbent. OR3 is a modified hydrophilic adsorbent comprising a spherical polar silica adsorbent having a high level of silenol (Si—O—H) groups, having an average particle diameter of between 60 and 200 microns, having a surface area of between 450 and 550 m²/g, having a pore volume of between 0.7 and 0.85 mL/g, and having a pore size of between 50 to 75 Angstroms (0.005-0.0075 microns). OR4 is an activated alumina adsorbent having an average particle diameter of between 50 and 200 microns, an average bulk density of 0.85 g/ml, a surface area of between 140-170 m²/g, and an average pore diameter of greater than 60 Angstroms (0.006 microns). The supernate non-polar solution in line 92 is passed sequentially through the first and second isolate chromatography columns (121, 122) to provide an isolate elute stream in line 96. The isolate elute stream comprises non-polar solvent, cannabidiol, and a minor amount of other cannabinoids. The isolate elute stream in line 96 is passed to a crystallization zone 124, wherein the isolate elute stream in line 96 is subjected to a freezer temperature of equal to or less than about −20° C. for a freezer period of about 24 to about 72 hours to permit primary high purity cannabidiol crystals, containing from about 96 to about 98 wt-% cannabidiol to form. The primary high purity cannabidiol (CBD) crystals are harvested and re-dissolved into a crystal isolate solution by admixing the primary high purity cannabidiol crystals with hexane to provide the crystal isolate solution comprising 20-30% by weight cannabidiol CBD oils. The crystal isolate solution is placed into stainless steel receptacles and allowed to stand at room temperature for a period of 24-72 hours to permit secondary high purity CBD crystals to again form. The secondary high purity CBD crystals formed, comprise about 99% CBD by weight. These secondary high purity CBD crystals are harvested and passed via line 98 to a rotary evaporation zone 126. In the rotary evaporation zone 126, the secondary crystals are heated until molten, and any residual hexane in the secondary high purity CBD crystals is evaporated. The secondary high purity CBD crystals typically melt at about 70° C., although the crystal melting point will vary depending upon the vacuum pressure in the flask of the rotary evaporator. Following evaporation of the hexane from the secondary high purity crystals, a third water wash stream introduced via line 99, using 200 g of water for every 1 Kg of secondary high purity crystals, is carried out in the rotary evaporation zone. Following the third water wash, any remaining water is removed by evaporation to complete dryness and the washed secondary high purity crystals are allowed to solidify to provide a solid CBD aggregate, which is essentially free of any detectable amount of THC. The solidification temperature is generally about 37° C. The solid CBD aggregate in line 130 was harvested. The solid CBD aggregate may be granulated or crushed into powder to provide a powdered CBD isolate product which is essentially free of THC. The resulting powdered CBD isolate is described by Tables 3 and 4. Table 3 describes the CBD purity of the isolate, while Table 4 describes the residual solvent analysis of the CBD isolate powder.

TABLE 3

CANNABINOID PROFILE OF ISOLATES

| Compound | Amount Reported |
|---|---|
| THC | 0 |
| THCV | 0 |
| CBG | 0 |
| CBD | 99.7% w/w |
| CBN | 0 |
| THCA | 0 |
| CBDA | 0 |
| CBDV | 0 |
| Other | 0.3 |

TABLE 4

RESIDUAL SOLVENT ANALYSIS OF CBD ISOLATES

| Solvent | Amount Reported |
|---|---|
| Ethanol | ND |
| Isopropanol | ND |
| Hexane | ND |
| Ethyl Acetate | ND |
| Heptane | ND |

Figure 2:
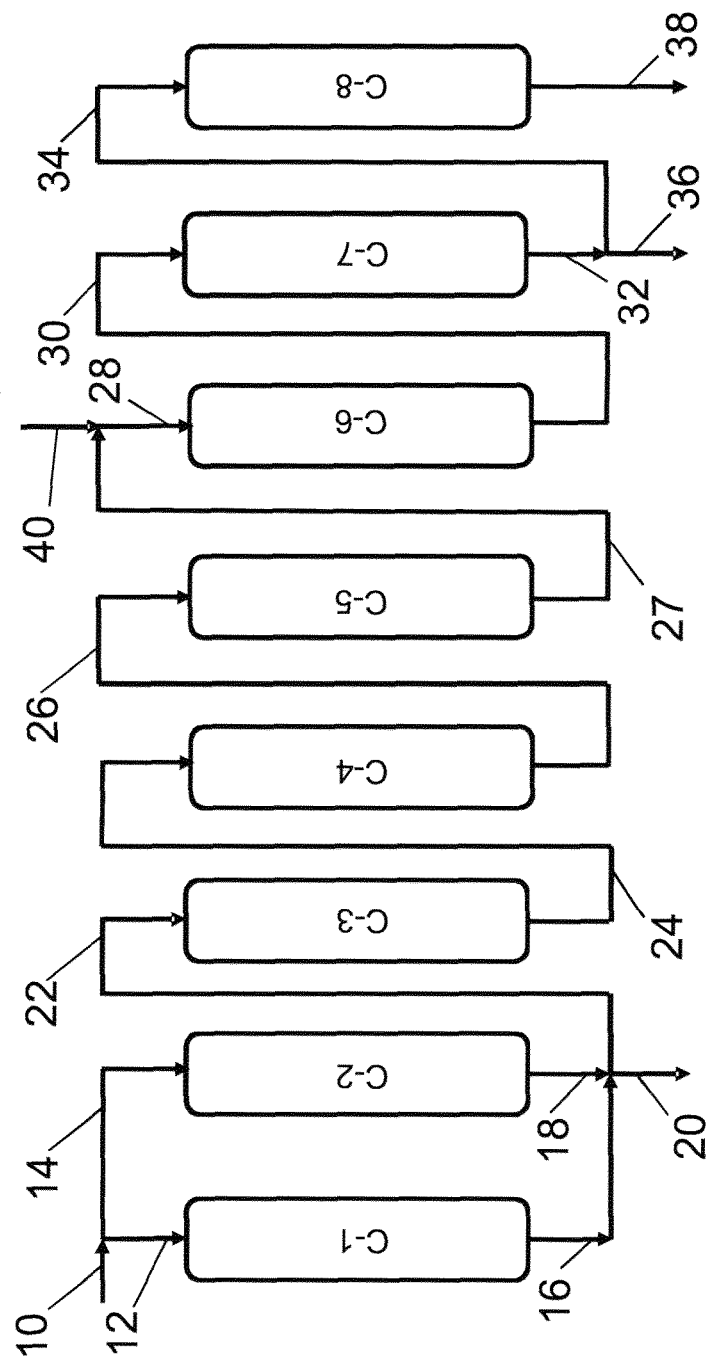
FIG. 2 is a schematic process flow diagram illustrating a configuration of the simulated moving bed cycle for a simulated moving bed zone in one embodiment of the invention.

According to one embodiment of the invention and with reference to FIG. 2, the simulated moving bed system is a continuous simulated moving bed system which continuously processes the dewaxed cannabinoid oil stream in line 10 to provide a primary raffinate stream in line 36. There were eight adsorption beds arranged in series and connected through a proprietary pneumatic valve array (not shown). The SMB scheme shown in FIG. 2 is a 2-3-2-1 arrangement, wherein 2 adsorbent beds (C-1, C-2) were operated in a desorption zone, 3 adsorbent beds (C-3, C-4, C-5) were operated in a rectification zone, 2 adsorbent beds (C-6, C-7) were operated in an adsorption zone, and 1 adsorbent bed (C-8) was operated in a concentration zone for raffinate. The independently working and programmable 72-valve array contains no moving parts, occupies only 3 μl per valve, and responds within 100 ms. Fluid flow is controlled by four independent pumps. The valve switching and pump flow rates are controlled via the SembaPro Software. The eight adsorbent beds (C-1, C-2, C-3, C-3, C-4, C-5, C-6. C-7, and C-8) were cylinders of 304 stainless steel, each adsorbent bed having an inside column diameter of 15 cm (6 inch) and a column length of 90 cm (36 inches), and each adsorbent bed contained about 10 Kg of OR2 adsorbent. The rotary valve system was operated on a cycle, wherein bed switching occurred at every 10-20 minute intervals. The eight adsorption beds were arranged in serial fluid communication such that fluid introduced at the top of any adsorbent bed n continued to the next highest adsorbent bed n+1 by passing the effluent from the bottom of adsorbent bed n to the top of adsorbent bed n+1. The adsorbent beds were operated in four zones, zone 1 (desorption), zone 2 (rectification), zone 3 (adsorption), and zone 4 (concentration), whereby the SMB feedstock stream, or dewaxed hemp oil stream, or cannabinoid oil stream in line 40 was loaded on to zone 3 (C-6) by introducing the SMB feedstock stream via lines 40 and 28 to adsorbent bed C-6. In zone 3, cannabidiol (CBD) was selectively adsorbed in adsorbent beds C-6 and C-7, and the primary raffinate stream was withdrawn in lines 32 and 36 from adsorbent bed C-7. The primary raffinate had with an average primary raffinate solids concentration of 5.0-7.0 g/L and an average cannabidiol (CBD) purity of 80-87% w/w and an average THC purity of 0.0% w/w. The primary raffinate in line 68 can be passed to an evaporation zone (not shown) to recover the solvent; and, following evaporation of the primary raffinate stream to dryness, provides a high purity cannabidiol (CBD) oil stream which is essentially free of THC. At least a portion of the primary raffinate steam in line 32 was passed to zone 4 comprising adsorbent bed C-8 in line 34 and a secondary raffinate stream was withdrawn from adsorbent bed C-8 in line 38. The secondary raffinate is withdrawn in line 38 at a very small flow rate compared to the flow rate of the primary raffinate flow rate and comprises essentially no cannabidiol (CBD) or THC oils. The secondary raffinate stream can be directly returned to zone 1 to offset the amount of the mobile phase desorbent in line 10. In the same step, a polar mobile phase desorbent in line 10, comprising an 80:20 volume mixture of ethanol and water, was simultaneously introduced to zone 1, comprising adsorbent beds C-1 and C-2, via lines 12 and 14, respectively. The mobile phase was passed through zone 1 in parallel through adsorbent beds C-1 and C-2, and the effluent of adsorbent beds C-1 and C-2 was withdrawn in lines 16 and 18, respectively, and combined to form an SMB extract stream in line 20. The SMB extract stream comprises the mobile phase desorbent, THC and CBD. The SMB extract stream line 20 is passed to a second evaporation zone for solvent recovery (not shown). A portion of the SMB extract stream in line 22 was passed to zone 2 (comprising adsorbent beds C-3, C-4, and C-5) and introduced to the top of adsorbent bed C-3, and continuing serially through adsorbent beds C-3, C-4, and C-5 via lines 24, and 26, respectively. The effluent withdrawn from the bottom of adsorbent bed C-5 was passed to the top of adsorbent bed C-6 in line 27, and admixed with the SMB feedstock stream in line 40 before being passed to adsorbent bed C-6 in line 28. At the completion of each SMB cycle, the adsorbent beds was advanced to move countercurrent to the SMB feedstock, whereby adsorbent bed C-2 shifts to the left to the position previously occupied by C-1 and C-1 was shifted to the position previously occupied by adsorbent bed C-8.

In another embodiment, the invention includes the steps of extracting crude *cannabis* from dry hemp leaves. The steps of the leaf extraction comprise:
i) combining dry hemp leaves with a first portion of food grade ethanol to provide a first leaf/solvent mixture and agitating the first leaf/solvent mixture;
ii) soaking the first leaf/solvent mixture for an effective soaking time to form a first ethanol layer;
iii) decanting the first ethanol layer to provide a first decant stream and a first portion of wet leaves;
iv) combining a second portion of food grade ethanol with the first portion of wet leaves to provide a second leaf/solvent mixture and agitating the second leaf/solvent mixture and decanting a second ethanol layer to provide a second decant stream and residual leaves; and,
v) pressing the residual leaves to provide a third decant stream and combining the first decant stream, the second decant stream and the third decant streams to provide the crude *cannabis* extract stream.

The leaf extraction process is carried out at atmospheric pressure and room temperature of about 25° C. The first leaf mixture is allowed to soak for an effective soaking time comprising about 8 to 12 hours. Preferably, the combined decant streams should have a solids concentration of between about 23 to about 30 g/Liter. More preferably the combined decant streams should have a maximum solids concentration less than about 30 g/Liter.

The following examples are provided to illustrate the present invention. These examples are shown for illustrative purposes, and any invention embodied therein should not be limited thereto.

EXAMPLES

Example 1—Extraction of *Cannabis* Leaves with Ethanol

Figure 3:
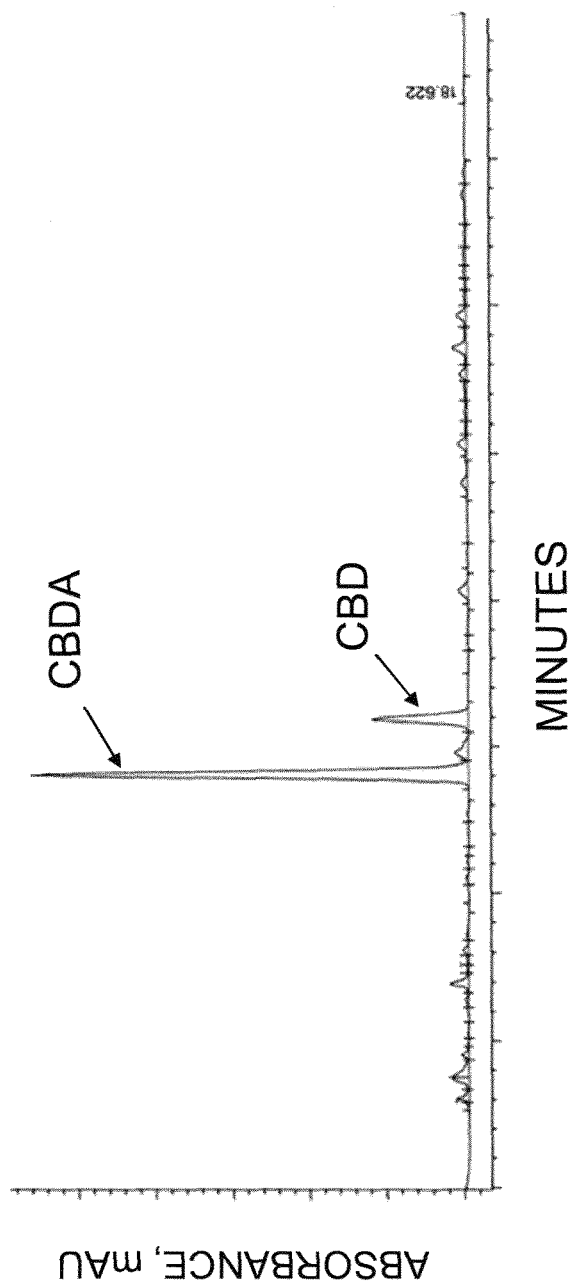
FIG. 3 is a High Performance Liquid Chromatography (HPLC) chromatographic area plot showing the results of a composition analysis of cannabinoids in the extract of dried hemp leaves.
Figure 8:
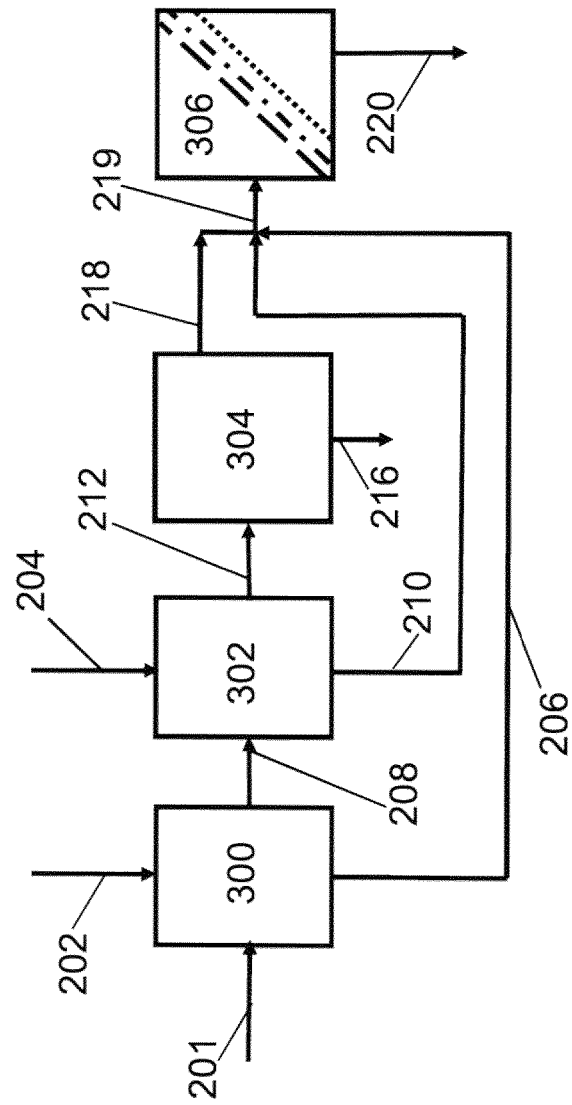
FIG. 8 is a schematic process flow diagram of the leaf extraction and filtration steps in one embodiment of the invention.

FIG. 8 is a schematic process flow diagram of the leaf extraction and filtration steps of the invention. With reference to FIG. 8, about 150 Kg of dried *cannabis* leaves, shown in 201, was added to a 1000 Liter tote 300 and about 600 Liters of food grade ethanol (200 proof) was introduced to the tote 300 via line 202 to create a leaf/solvent mixture. The leaf/solvent mixture was agitated using a pneumatic mixer for a period of two hours at room temperature of about 25° C. at atmospheric pressure and allowed to stand overnight for an effective time (about 8 to 12 hours) to form a first ethanol layer. The first ethanol layer over the wet leaves was removed as a first decant stream in line 206. Shown as a second extraction step in tote 302, which may physically be the same as tote 300. A second portion of ethanol comprising 400 Liters of food grade ethanol was introduced via line 204 and again the leaf/solvent mixture was agitated in a second mixing step using a pneumatic mixer for a period of two hours at room temperature of about 25° C. at atmospheric pressure in a second extraction step. At the conclusion of the second mixing step, a second decant stream in line 210 was withdrawn and the remaining wet leaves were passed to a screw type extraction press (VINCENT Model CP10 available from Vincent Corporation, Tampa, Fla.) wherein the solids were pressed or squeezed, resulting in a third liquid decant stream in line 218 and used or spent leaves. The used or spend leaves shown as stream 216 are withdrawn and passed to waste disposal. The first, second and third decant streams (206, 210 and 218) were combined and passed to a filtration zone 306 as a liquid leaf extract stream in line 219. Following extraction the solid concentration of the liquid leaf extract stream comprised of 35-40% cannabidiol and cannabidiolic acid. The solid concentration of total solids (as measured following evaporation of the solvent from the liquid leaf extract stream) in the liquid leaf extract stream was approximately 25-30 g/L. The liquid leaf extract stream or crude *cannabis* extract stream was decanted and filtered in the filtration zone 306 to remove solid particles, by passing the liquid leaf extract stream through three successive filters of decreasing pore size: 100 micron, 20 micron, and 10 micron. The 100 micron pore size filter comprised a bag made of felt for high capacity flow and capturing solids. The 20 and 10 micron pore size filters were cartridges comprising polyethylene and were pleated for higher surface area. The cartridges had O-rings on a fitting at the end for seating inside a stainless steel cylindrical housing. The filtered liquid leaf extract stream was green in color, was essentially free of particles, and comprised approximately 20-40 g/L of cannabidiol (CBD) and cannabidiolic acid (CBDA). FIG. 3 illustrates a High Performance Liquid Chromatography (HPLC) chromatographic area plot showing the results of a composition analysis of cannabinoids in the filtered liquid extract stream. Table 5 shows the composition of the filtered liquid extract stream or filtered crude cannabinoid stream from the extract of industrial hemp leaves.

TABLE 5

Extracted Material from Industrial Hemp Leaves

| Compound | Amount Reported, wt-% |
|---|---|
| THC | 0.1 |
| THCV | 0.0 |
| CBG | 1.0 |
| CBD | 4.0 |
| CBN | 1.0 |
| THCA | 1.8 |
| CBDA | 25.0 |
| CBDV | 0.0 |
| Other | 67.1 |
| Total | 100.0 |

Example 2

Removal of Chlorophylls and Other Impurities

Figure 4:
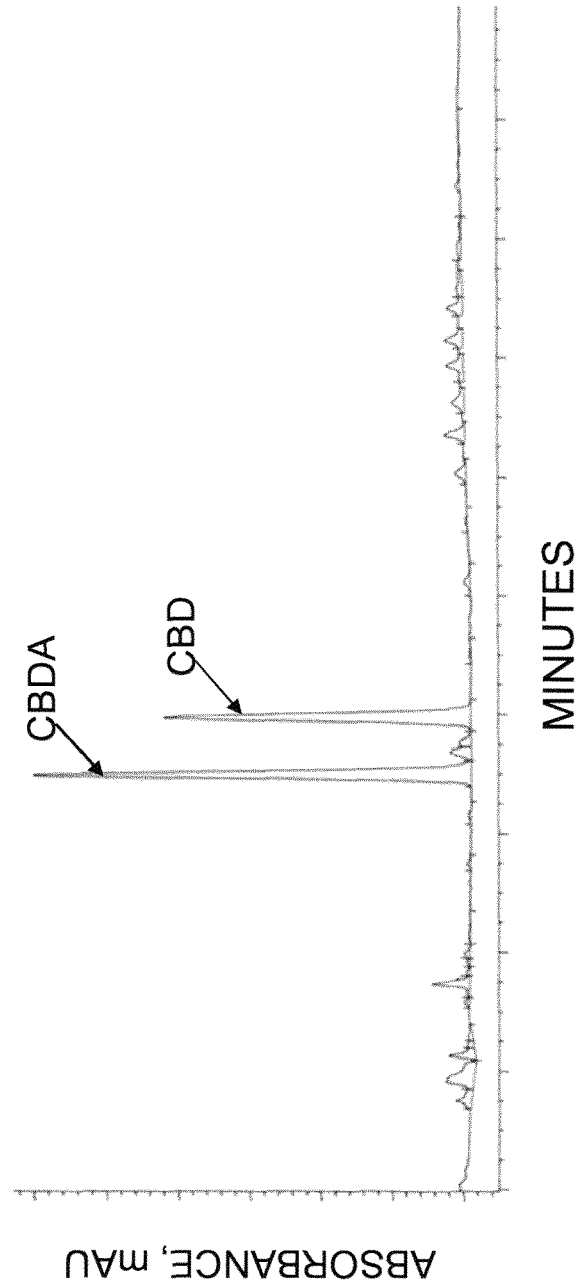
FIG. 4 is a High Performance Liquid Chromatography (HPLC) chromatographic area plot showing the results of a composition analysis of the cannabinoids in decolorized extract.

The green, filtered liquid extract stream, or filtered crude cannabinoid stream of Example 1 was loaded into a column chromatography zone to remove chlorophylls and other impurities. The filtered liquid leaf extract stream was passed through a 10 um filter to the top of a decolorization chromatographic column. The decolorization chromatographic column was comprised of polypropylene, having an inside diameter of 60 cm and a length of 183 cm (24 inches by 72 inches) and having an internal volume of 450 L (119 gal). The column was operated at a decolorization pressure of 2.72 atm to about 4.08 atm (40-60 psig) and a decolorization temperature ranging from 20-25° C. The flow rate used for the decolorization chromatographic column was between 2-3 L/min. The decolorization chromatographic column was packed with OR1 adsorbent. OR1 is a modified activated carbon adsorbent which was heat treated to provide a highly hydrophobic adsorbent which is essentially free of hydroxyl groups, and has an average particle diameter of between 177 and 250 microns, and an iodine number (a measure of the micropore content of the activated carbon) of above 900 mg/g. Essentially all chlorophylls were removed from the filtered liquid extract stream, and the resulting concentration of the solids in the extract stream was about 40-45% cannabidiol (CBD) and cannabidiolic acid (CBDA) and the concentration of total solids in the stream was approximately 20-35 g/L concentration. An HPLC trace of cannabinoids present within decolorized hemp leaf extract, or decolorized crude extract stream is shown in FIG. 4. In FIG. 4, the cannabidiol (CBD) and cannabidiolic acid (CBDA) composition peaks are essentially unchanged from FIG. 3. Thus, no chemical change occurred during the decolorization process, however the color observed in the resulting decolorized extract stream changed from green to amber. Table 6 shows the composition of the decolorized extract stream.

TABLE 6

Composition of Decolorized Extract Stream

| Compound | Amount Reported, wt-% |
|---|---|
| THC | 0.11 |
| THCV | 0.0 |
| CBG | 1.1 |
| CBD | 4.4 |
| CBN | 1.1 |
| THCA | 1.98 |
| CBDA | 35.0 |
| CBDV | 0.0 |
| Other | 63.81 |
| Total | 100.00 |

Example 3

Activation or Conversion of CBDA in to CBD and THCA into THC

Figure 5:
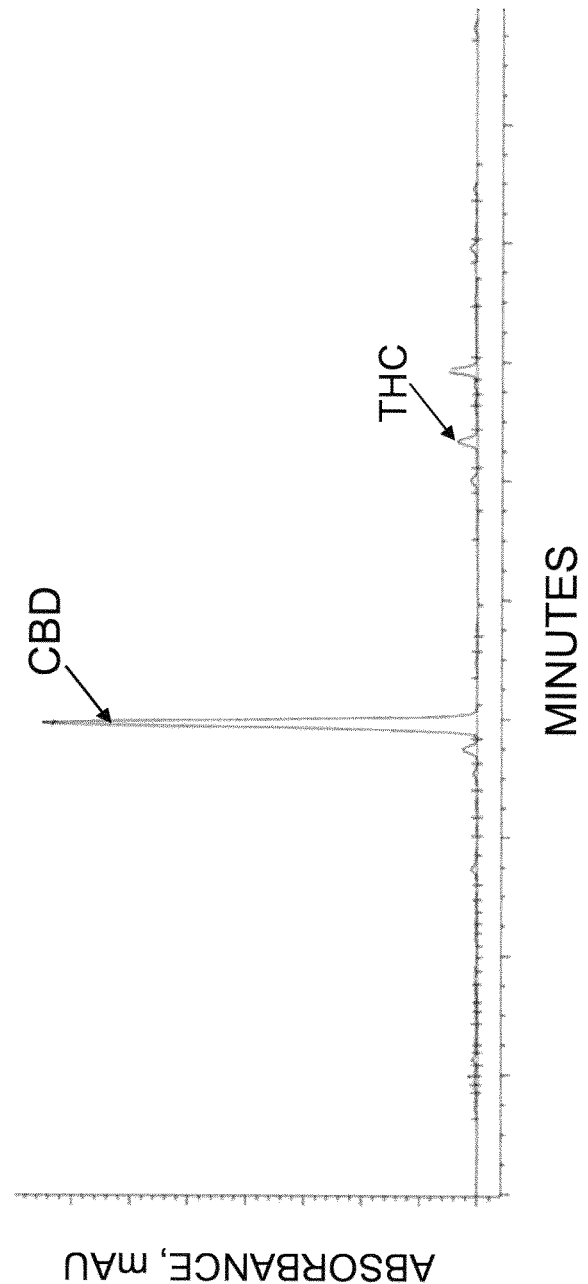
FIG. 5 is a High Performance Liquid Chromatography (HPLC) chromatographic area plot showing the results of a composition analysis of cannabinoids in activated extract.

The decolorized hemp leaf extract stream prepared in Example 2 was passed to a vacuum distillation unit, to remove essentially all of the solvent from the mixture. The vacuum distillation condenser had a 240 L capacity. This unit was operated at a vacuum pressure of −0.602 to −0.735 atm (−18 to −22 in Hg) and a temperature of 90-110° C. At least a portion of ethanol solvent recovered from the vacuum distillation unit was reused as solvent for the hemp leaf extraction step, described in Example 1. Following removal of the solvent, the resulting oil was retained in the vacuum distillation vessel at a decarboxylation temperature of 90 to 120° C. and a decarboxylation pressure of about −0.6 to 0.74 atm for an additional 5 to 8 hours, to permit sufficient time for the decarboxylation reaction to occur. The decarboxylation reaction time was sufficient to fully decarboxylate essentially all of the acidic components to provide a decarboxylated hemp oil. During the course of the decarboxylation reaction it was observed that some of the impurities in the feed were aggregated into a sludge like material which floated on top of the decarboxylated hemp oil. The aggregated impurities were removed, by subjecting the decarboxylated hemp oil to a water wash step to solubilize the impurities and remove the impurities from the decarboxylated hemp oil. FIG. 5 is an HPLC trace of cannabinoids present within decarboxylated hemp oil. In FIG. 5. A CBD peak was observed, but there was no CBDA peak present. The absence of a CBDA peak showed that the decarboxylation reaction of CBDA to CBD has proceeded to completion. The THC peak appears more prominently in FIG. 5 than before, which indicates that any THCA, although present in very small amounts in the decarboxylated hemp oil, has also been converted to THC. Table 7 shows the composition of the activated or decarboxylated cannabinoid oil stream.

TABLE 7

Composition of Decarboxylated Cannabinoid Oil

| Compound | Amount Reported, wt-% |
|---|---|
| THC | 2.09 |
| THCV | 0.0 |
| CBG | 1.1 |
| CBD | 40.0 |
| CBN | 1.1 |
| THCA | 0.0 |
| CBDA | 0.0 |
| CBDV | 0.0 |
| Other | 55.41 |
| Total | 100.00 |

Example 4

Dewaxing and Impurity Removal from Decarboxylated Hemp Oil

Figure 6:
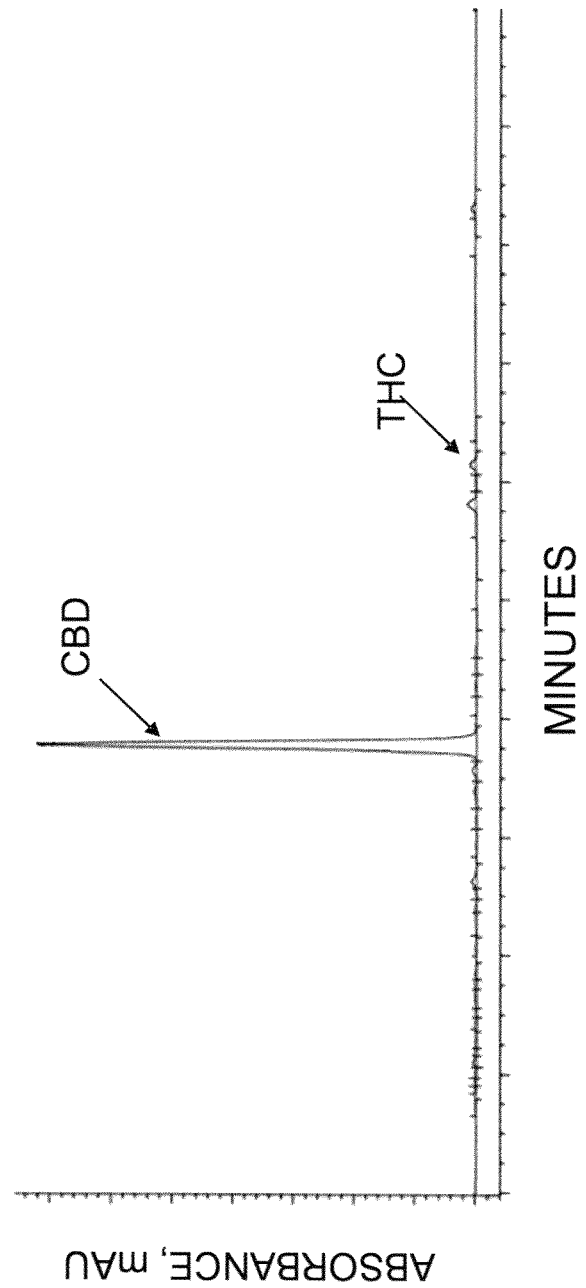
FIG. 6 is a High Performance Liquid Chromatography (HPLC) chromatographic area plot showing the results of a composition analysis of cannabinoids in dewaxed activated extract.

In the dewaxing zone, lipids and plant waxes were removed from the dewaxing feed stream. The decarboxylated hemp oil of Example 3 was reconstituted in a dewaxing solution containing ethanol and water in a volume ratio of 80/20 (Combine 800 cc of alcohol to 200 cc to prepare 1 Liter of dewaxing solvent) to provide a dewaxing feed stream having 40-45 g/L concentration of total solids. It was discovered that it was critical that the concentration of solids in the dewaxing feed stream not exceed 50 g/L of concentration. The dewaxing feed stream was passed to the top of a dewaxing column at a dewaxing flow rate of 2-3 L/min and a dewaxing column pressure of 2.72 to 4.08 atm (40-60 psi) and room temperature (20-25° C.). The dewaxing column was comprised of polypropylene, having an inside diameter of 60 cm and a length of 183 cm (24 inches by 72 inches) and having an internal volume of 450 L (119 gal). The dewaxing column was packed with OR1 adsorbent. OR1 is a modified activated carbon adsorbent which was heat treated to provide a highly hydrophobic adsorbent which is essentially free of hydroxyl groups, and has an average particle diameter of between 177 and 250 microns, and an iodine number (a measure of the micropore content of the activated carbon) of above 900 mg/g. The effluent from the dewaxing column, or dewaxed hemp oil stream had a concentration of total solids in the dewaxed hemp oil stream of from 35 to 40 g/L, and comprised of about 60 wt-% cannabidiol. FIG. 6 shows the cannabinoid makeup of the dewaxed hemp oil stream. In FIG. 6, the concentration of tetrahydrocannabinol (THC) is significantly reduced compared to the amount of THC in the decarboxylated hemp oil as shown in FIG. 5. Table 8 shows the composition of the dewaxed cannabidiol oil.

TABLE 8

Composition of Dewaxed Cannabidiol Oil

| Compound | Amount Reported, wt-% |
|---|---|
| THC | 2.0 |
| THCV | 0.0 |
| CBG | 1.1 |
| CBD | 55.0 |
| CBN | 1.1 |
| THCA | 0.0 |
| CBDA | 0.0 |
| CBDV | 0.0 |
| Other | 40.8 |
| Total | 100.0 |

Example 5

THC Removal and CBD Enrichment by SMB Process

The simulated moving bed (SMB) process step for the removal of THC from a mixture of THC and CBD in the dewaxed hemp oil stream was demonstrated in a specially configured eight-bed SMB system for reversed phase separation. A lab scale SMB unit (OCTAVE-300 unit, available from Semba Biosciences, Inc., Madison, Wis.) was used for the separation and was configured as shown in FIG. 2. The Semba Octave-300 Chromatography System is a bench top automated liquid chromatography platform designed for preparative-scale purification of chemical and biological compounds. According to FIG. 2, there were eight adsorption beds arranged in series and connected through a proprietary pneumatic valve array (not shown). The SMB scheme shown in FIG. 2 is a 2-3-2-1 arrangement, wherein 2 adsorbent beds (C-1, C-2) were operated in a desorption zone, 3 adsorbent beds (C-3, C-4, C-5) were operated in a rectification zone, 2 adsorbent beds (C-6, C-7) operated in an adsorption zone, and 1 adsorbent bed (C-8) is operated in a concentration zone for raffinate. The independently working and programmable 72-valve array contains no moving parts, occupies only 3 µl per valve, and responds within 100 ms. Fluid flow is controlled by four independent pumps. The valve switching and pump flow rates are controlled via the SembaPro Software. The eight adsorbent beds (C-1, C-2, C-3, C-3, C-4, C-5, C-6. C-7, and C-8) were cylinders of 304 stainless steel, each adsorbent bed having an inside column diameter of 22 mm and a column length of 300 mm, and each adsorbent bed contained about 51.3 grams of adsorbent OR2. OR2 was modified hydrophobic adsorbent comprising a styrene-divinylbenzene (DVB) resin having 4 to 8 percent crosslinking or a poly(methyl methacrylate) (PMMA) resin. The OR2 hydrophobic adsorbent had an average particle diameter of between 25 and 300 microns, an average bulk density (gm/mL) of from 0.4 to 0.6, a surface area (m2/g) of from 450 to 550, and a pore volume of from 0.70-0.90 (mL/g) The rotary valve system was operated on a cycle, wherein bed switching occurred at every 10-20 minute intervals. The eight adsorption beds were arranged in serial fluid communication such that fluid introduced at the top of any adsorbent bed n continued to the next highest adsorbent bed n+1 by passing the effluent from the bottom of adsorbent bed n to the top of adsorbent bed n+1. The adsorbent beds were operated in four zones, zone 1, zone 2 zone 3, and zone 4, whereby the SMB feedstock stream, or dewaxed hemp oil stream in line 40 was loaded on to zone 3 (C-6) by introducing the SMB feedstock stream via lines 40 and 28 to adsorbent bed C-6. In zone 3, CBD was selectively adsorbed in adsorbent beds C-6 and C-7, and a primary raffinate stream was withdrawn in lines 32 and 36 from adsorbent bed C-7. At least a portion of the primary raffinate steam in line 32 was passed to zone 4 comprising adsorbent bed C-8 in line 34 and a secondary raffinate stream was withdrawn from adsorbent bed C-8 in line 38. The secondary raffinate comprised essentially no CBD or THC oils and was directly returned to zone 1 to offset the amount of the mobile phase desorbent in line 10. The flow rate of the secondary raffinate was about 2 wt-% of the flow rate of the primary raffinate. In the same step, a polar mobile phase desorbent in line 10, comprising an 80:20 volume mixture of ethanol and water, was simultaneously introduced to zone 1, comprising adsorbent beds C-1 and C-2, via lines 12 and 14, respectively. The mobile phase was passed through zone 1 in parallel through adsorbent beds C-1 and C-2, and the effluent of adsorbent beds C-1 and C-2 was withdrawn in lines 16 and 18, respectively, and combined to form an SMB extract stream in line 20. A portion of the SMB extract stream in line 22 was passed to zone 2 (comprising adsorbent beds C-3, C-4, and C-5) and introduced to the top of adsorbent bed C-3, and continuing serially through adsorbent beds C-3, C-4, and C-5 via lines 24, and 26, respectively. The effluent withdrawn from the bottom of adsorbent bed C-5 was passed to the top of adsorbent bed C-6 in line 27, and admixed with the SMB feedstock stream in line 40 before being passed to adsorbent bed C-6 in line 28. At the completion of each SMB cycle, the adsorbent beds was advanced to move countercurrent to the SMB feedstock, whereby adsorbent bed C-2 shifts to the left to the position previously occupied by C-1 and C-1 was shifted to the position previously occupied by adsorbent bed C-8.

SMB Feed

The decarboxylated hemp oil stream of Example 4 was admixed with an 80:20 mixture of water and food grade ethanol to provide an SMB feedstock stream having 40-60 w/w % CBD purity and 0.4-1.0 w/w % THC purity. The SMB feedstock stream was passed at an average SMB flow rate of 0.15-0.30 L/min to a guard column of 304 stainless steel. The guard column was cylindrical and had an inside column diameter of 15 cm (6 inch) and a column length of 90 cm (36 inches). The guard column was packed with OR2 adsorbent. OR2 is modified hydrophobic adsorbent comprising a styrene-divinylbenzene (DVB) resin having 4 to 8 percent crosslinking or a poly(methyl methacrylate) (PMMA) resin. The OR2 hydrophobic adsorbent has an average particle diameter of between 25 and 300 microns, an average bulk density (gm/mL) of from 0.4 to 0.6, a surface area (m2/g) of from 450 to 550, and a pore volume of from 0.70-0.90 (mL/g). The guard column provides some additional color removal and also removes any particulates from the SMB feedstock prior introducing the SMB feedstock to the SMB zone. The guard column was cleaned and regenerated regularly, about every 1 to 2 weeks. After being passed through a guard column, and with reference to FIG. 2, the SMB feedstock in line 40 was passed to the top of adsorbent bed C-6 via lines 40 and 28.

Mobile Phase Desorbent

The mobile phase desorbent used in the SMB zone was a mixture of ethanol in water. The ethanol was Food Grade Ethanol (Proof 200) and the water was deionized water. The mobile phase desorbent comprised a ratio of ethanol:water of 80:20 volume/volume. The mobile phase desorbent, with reference to FIG. 2, in line 10 passed to the tops of adsorbent beds C-1 and C-2 at a desorbent rate 2.0-3.0 L/min.

Stationary Phase

The stationary phase adsorbent in the SMB zone was OR2. OR2 is modified hydrophobic adsorbent comprising a styrene-divinylbenzene (DVB) resin having 4 to 8 percent crosslinking or a poly(methyl methacrylate) (PMMA) resin. The OR2 hydrophobic adsorbent had an average particle diameter of between 25 and 300 microns, an average bulk density (gm/mL) of from 0.4 to 0.6, a surface area (m2/g) of from 450 to 550, and a pore volume of from 0.70-0.90 (mL/g)

Process Parameters

The operating parameters of the SMB zone are shown in Table 9

TABLE 9

SMB Operating Parameters

| PARAMETER | VALUE | UNIT |
|---|---|---|
| Step Time | 10-20 | Minutes |
| Temperature | 20-25 | ° C. |
| Feed Rate (line 40)* | 0.23-0.50 | L/Min |
| Desorbent (line 12) | 1.27-2.0 | L/Min |
| Desorbent (line 14) | 1.27-2.0 | L/Min |
| Zone 2 Return (line 22) | 0.92-1.50 | L/Min |
| Extract (line 16) | 1.27-2.0 | L/Min |
| Extract (line 18) | 1.27-2.0 | L/Min |
| Primary Raffinate (line 36) | 0.99-1.50 | L/Min |
| Secondary Raffinate (line 38) | 0.16-0.25 | L/Min |

*Line numbers refer to FIG. 2

Figure 7:
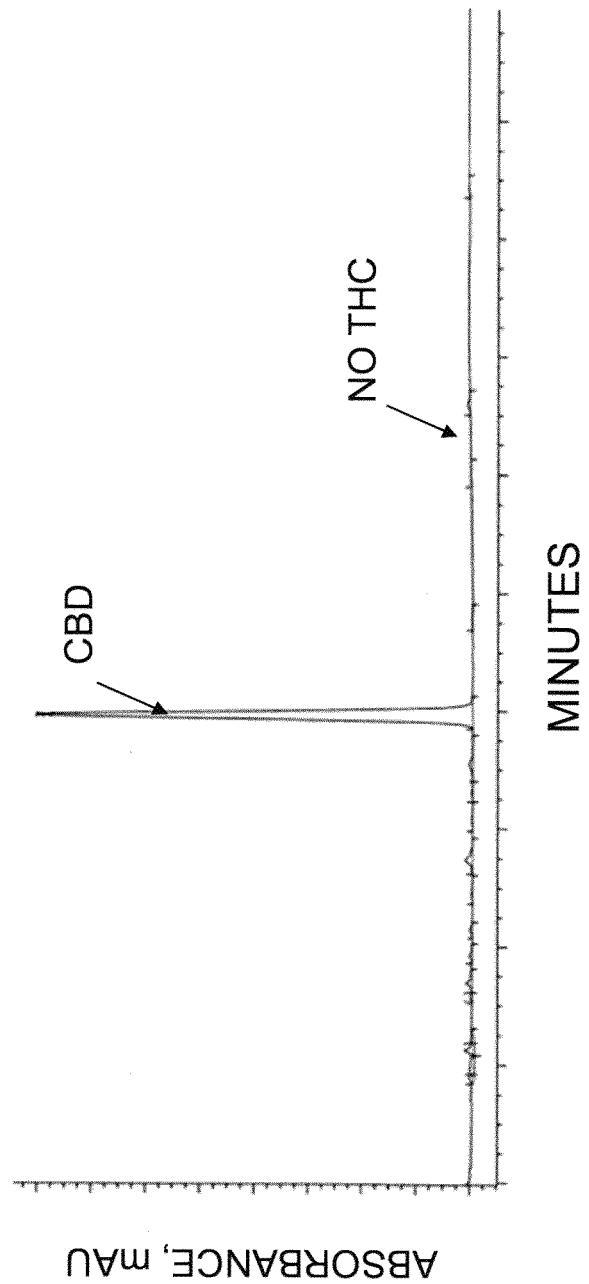
FIG. 7 is a High Performance Liquid Chromatography (HPLC) chromatographic area plot showing the results of a composition analysis of cannabinoids in polished activated extract.

The primary raffinate, withdrawn in line 36 was withdrawn at an average flow rate of 1.0-3.0 L/min. The primary raffinate had with an average concentration of solids of 5.0-7.0 g/L and an average CBD purity of 80-87% w/w and an average THC purity of 0.0% w/w, The primary raffinate was passed to an evaporation zone to recover the solvent and, following evaporation of the primary raffinate to dryness provides a THC free CBD oil stream which is essentially free of THC. FIG. 7 is an HPLC trace of the THC free CBD oil stream which shows the presence of CBD and the absence of any THC. The extract stream, withdrawn in line 20 was withdrawn at a rate of 1.0-2.0 g/L and comprised an average cannabinoid CBD purity of 35-40 w/w % and an average THC purity of 15-24 w/w %. A portion of the extract was passed to the top of zone 2 (C-3) at a rate of 1.0-2.0 L/min.

In a representative example of the SMB process described hereinabove, with a mobile phase desorbent comprising 80 vol-% ethanol:20 vol-% water; and an SMB feed rate of 11.66 Kgs per day of dewaxed cannabidiol oil having 55.0 wt-% CBD and 2.0 wt-% THC (See Table 8, hereinabove) the primary raffinate stream was withdrawn at a rate of 9.3 Kgs per day and comprised 65.0 wt-% CBD and 0.0 wt-% THC; the extract stream was withdrawn at a rate of 2.3 Kgs per day and comprised 14.35 wt-% CBD and 10.12 wt-% THC; and, the secondary raffinate was withdrawn at a rate of 0.098 Kgs per day and comprised 39.0 wt-% CBD and 0.30 wt-% THC. All of the above percentages were expressed on a solvent free basis. The compositions of the primary raffinate stream, the secondary raffinate stream and the extract stream were determined on a solvent free basis. The unreported portion of these streams was considered to be other cannabinoids. The primary raffinate composition following solvent removal is shown in Table 10.

TABLE 10

Composition of Primary Raffinate (Solvent Free Basis)

| Compound | Amount Reported, wt-% |
|---|---|
| THC | 0.00 |
| THCV | 0.0 |
| CBG | 0.1 |
| CBD | 65.0 |
| CBN | 0.1 |
| THCA | 0.0 |
| CBDA | 0.0 |
| CBDV | 0.0 |
| Other | 34.8 |
| Total | 100.0 |

Example 6

Polishing Step

In a polishing step, the dewaxed hemp oil stream of Example 4, wherein the lipids and plant waxes were removed, was passed to a polishing chromatography column. The polishing chromatographic column was comprised of polypropylene, having an inside diameter of 60 cm and a length of 183 cm (24 inches by 72 inches) and having an internal volume of 450 L (119 gal). The column was operated at a polishing pressure of 2.72 atm to about 4.08 atm (40-60 psig) and a polishing temperature ranging from 20-25° C. The flow rate used for the polishing chromatographic column was between 2-3 L/min. The polishing chromatographic column was packed with OR1 adsorbent.

OR1 was a modified activated carbon adsorbent which was heat treated to provide a highly hydrophobic adsorbent which is essentially free of hydroxyl groups, and has an average particle diameter of between 177 and 250 microns, and an iodine number (a measure of the micropore content of the activated carbon) of above 900 mg/g. Dewaxed extract was passed to the polishing chromatography column and the eluent stream was observed for the breakthrough of tetrahydrocannabinol (THC). Once THC breakthrough was observed using high performance liquid chromatography (HPLC), the passing of the dewaxed hemp oil stream was discontinued, and the effluent of the polishing chromatography column was collected to provide a CBD polished oil stream. The CBD polished oil stream withdrawn from the polishing chromatography column comprised no THC and comprised a cannabidiol (CBD) concentration of about 70-75% on a solvent free, dry weight basis. The concentration of total solids in the effluent of the polishing chromatography column was about 15-30 g/L. Like the THC free CBD oil stream from the SMB zone, an HPLC chromatogram of the showed no peak for THC. An HPLC analysis of the effluent of the polishing chromatography column showed a large quantity of CBD was present, thus indicating that the majority of the sample was CBD. There were also other terpenes and minor cannabinoids present in the oil that were not THC or CBD.

Example 7 CBD Enrichment by Removing Polar Compounds

The CBD polished oil stream of Example 6 was further processed to remove polar impurities. Although, after the polishing step, the purity of CBD in the material is already high, this step increased the CBD purity by another 5-10% in the CBD polished oil stream, resulting in 80-85% CBD purity. The CBD polished oil stream was passed to a first evaporation zone wherein the solvent was evaporated. The product stream was passed to a vacuum distillation vessel which was operated at a first evaporation zone temperature of about 80-100° C. and a first evaporation zone pressure of −0.53 to −0.67 atm (−16 to −20 in Hg). Following evaporation of the solvent, the remaining oil portion was re-dissolved to provide a non-polar solution using hexane as a non-polar solvent. In normal operation, about 30 Kg of the remaining oil portion from the evaporated CBD polished oil stream was added to 100 L of hexane. The normal yield of polished CBD oil was about 90-95 wt-% of the polished oil material passed to the first evaporation zone. The purity of the polished CBD oil after removal of the polar impurities generally increased by about 5 wt-%). Table 11 shows the effect of the polishing step on the CBD oil.

TABLE 11

Effect of Polishing Step on CBD Oil Purity

| | Starting material | Resulting material in solution |
|---|---|---|
| Weight | 30 Kg | 27-28 Kg |
| Hexane Volume | 0 L | 100 L |
| CBD Purity | 75-80% | 80-85% |

The solution was prepared at a concentration of 10-30% by weight. The solution was agitated and allowed to rest at room temperature for a period of 120 to 720 minutes to allow the polar compounds to settle out. The supernatant hexane solution was decanted to remove solution comprising the CBD oil from the solid polar compounds that had precipitated.

Example 8

Preparation of Phytocannabinoid Rich Oil:

The supernatant hexane solution of Example 7 was passed to a second evaporation zone to remove all of the polar solvent, hexane. The second evaporation zone used a rotary evaporator operating at a second evaporator temperature of about 35-45° C., a second evaporator pressure of about 0 to about −0.0148 atm (0-15 mbar vacuum), for a second evaporator time of about 2-3 hours). The polar solvent, hexane, was evaporated and an evaporated CBD oil was recovered. The evaporated CBD oil was washed with ethanol, three times using an ethanol wash stream comprising food grade ethanol in washing ratio of 1:3 Liters of ethanol to Kg of oil ratio for each wash. After the ethanol wash, the oil was washed in a water wash step with water using a water wash ratio of 1:3 Liters of water to Kg of oil. Washes were carried out inside the flask of the rotary evaporator and the resulting solutions were evaporated to complete dryness after each wash to provide a THC free Phytocannabinoid rich oil product. The resultant THC free Phytocannabinoid rich oil is described in Tables 12 and 13, where Table 12 describes the range of composition of the cannabinoids in the Phytocannabinoid Rich Oil, and Table 13 describes the residual solvent analysis in the Phytocannabinoid Rich Oil. No detectable solvent was found to present in the THC free Phytocannabinoid rich oil product as described in Table 13.

TABLE 12

THC free Cannabinoid profile of Phytocannabinoid Rich Oil

| Compound | Amount reported % |
|---|---|
| THC | 0 |
| THCV | 0 |
| CBG | 0-4% |
| CBD | 70-86% |
| CBN | 0-3% |
| THCA | 0 |
| CBDA | 0 |
| CBDV | 0-1% |
| Other | 30-10% |

TABLE 13

Residual Solvent Analysis of THC free Phytocannabinoid Rich Oil

| Solvent | Amount Reported |
|---|---|
| Ethanol | ND |
| Isopropanol | ND |
| Hexane | ND |
| Ethyl Acetate | ND |
| Heptane | ND |

ND - None-Detected

Example 9

Preparation of CBD Isolate:

The supernatant hexane solution of Example 7 can also be processed to provide a CBD isolate product. The CBD isolate product was prepared by passing the supernate hexane solution to an isolate chromatography zone comprising two isolate chromatographic columns connected in serial fluid communication. Each chromatographic column was filled with a selective adsorbent. The adsorbent in the first chromatographic column was OR3, and the adsorbent in the second chromatographic column was OR4, and the total mass of adsorbent in both the first and the second chromatographic columns determined the total amount of supernatant hexane solution which could be loaded. The two adsorbents OR3 and OR4 are described hereinabove. The amount of supernatant hexane solution passed to the isolate chromatography zone was determined by the amount of CBD material in the supernatant solution and the total mass of the two adsorbents; that is, 12-16 Kg of CBD material per Kilogram of the total mass of the two adsorbents (OR3 and OR4) of the supernatant hexane solution was passed a first of two isolate chromatographic columns. As supernatant hexane solution was passed to the columns the resulting isolate elute solution was collected. The resulting isolate elute solution, comprised about 20-30% of CBD oil by weight. The resulting isolate elute solution was placed into stainless steel receptacles and placed inside a freezer at a freezer temperature of −20° C. for a freezer period of 24-72 hours. In the freezer, at the freezer temperature was maintained below about −20° C., and high purity CBD crystals, containing 96-98% CBD by weight were formed. The high purity CBD crystals were harvested and re-dissolved into a crystal isolate solution with hexane and comprising 20-30% by weight CBD oils. The crystal isolate solution was placed into stainless steel receptacles and allowed to stand at about room temperature for a period of 24-72 hours. High purity CBD crystals formed, comprising about 99% CBD by weight. These high purity CBD crystals were harvested and placed inside of a flask of a rotary evaporator. The crystals were heated until molten, and the residual hexane was evaporated. The high purity CBD crystals typically melted at about 70° C., although the crystal melting point varied depending upon the vacuum pressure in the flask of the rotary evaporator. Following evaporation of the hexane from the high purity CBD crystals, a water wash, using 200 g of water for every 1 Kg of crystals to be washed, was carried out in the evaporator flask of the rotary evaporator. Following the water wash, the evaporation continued until any remaining water was removed by evaporation to complete dryness; and, the CBD isolate was allowed to solidify. The solidification temperature was about 37° C. The solidified CBD isolate was harvested and crushed into powder to provide a powdered CBD isolate. The resulting powdered CBD isolate is described hereinbelow in Tables 14 and 15. Table 14 describes the CBD purity of the isolate, while Table 15 describes the residual solvent analysis of the CBD isolate powder

TABLE 14

CANNABINOID PROFILE OF ISOLATES

| Compound | Amount Reported, wt-% |
|---|---|
| THC | 0 |
| THCV | 0 |
| CBG | 0 |
| CBD | 99.7 |
| CBN | 0 |
| THCA | 0 |
| CBDA | 0 |
| CBDV | 0 |
| Other | 0.3 |
| Total | 100.0 |

TABLE 15

RESIDUAL SOLVENT ANALYSIS OF CBD ISOLATES

| Solvent | Amount Reported |
|---|---|
| Ethanol | ND |
| Isopropanol | ND |
| Hexane | ND |
| Ethyl Acetate | ND |
| Heptane | ND |

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims, while the description, abstract and drawings are not to be used to limit the scope of the invention. The invention is specifically intended to be as broad as the claims below and their equivalents.

We claim:

1. A process for the purification of cannabidiol (CBD) in a crude *cannabis* extract stream to provide at least one high purity cannabidiol product selected from the group consisting of a high purity cannabinoid oil stream, a phytocannabinoid rich oil, a solid CBD aggregate and mixtures thereof being essentially free of tetrahydrocannabinol, said process comprising:
 a) passing the crude *cannabis* extract stream comprising debris and small particles, cannabidiol, tetrahydrocannabinol, cannabidiolic acid, tetrahydrocannabinolic acid, other cannabinols, chlorophylls, color bodies, sugars and carbohydrates, lipids, plant waxes, impurities, and ethanol to a first filtration zone comprising a series of successive filters of decreasing pore size, starting at a pore size of 100 microns and reducing to about 10 microns in 3 or more stages to remove debris and small particles in a progressive filtration step to provide a filtered crude cannabinoid stream;
 b) passing the filtered crude cannabinoid stream comprising cannabidiol, tetrahydrocannabinol, cannabidiolic acid, tetrahydrocannabinolic acid, other cannabinols, chlorophylls, color bodies, sugars and carbohydrates, lipids, plant waxes, impurities, and ethanol to a decolorization zone comprising a 10 μm filter and a decolorization chromatographic column containing a modified activated carbon adsorbent which was heat treated to provide a highly hydrophobic adsorbent which is essentially free of hydroxyl groups, has an average particle diameter of between 177 and 250 microns, and an iodine number of above 900 mg/g and operated at a decolorization pressure of 2.72 atm to about 4.08 atm (40-60 psig) and a decolorization temperature ranging from 20-25° C. to remove at least a portion of color bodies and essentially all of the chlorophyll to provide a decolorized extract stream;
 c) passing the decolorized extract stream to a first evaporation zone operated at a first vacuum pressure of −0.60 to about −0.74 atm (−18 to −22 in Hg) and a temperature of about 90 to about 110° C. to remove at least a portion of the ethanol to provide an evaporated extract stream which is essentially free of ethanol;

d) passing the evaporated extract stream comprising cannabidiol (CBD), cannabidiolic acid (CBDA), tetrahydrocannabinolic acid (THCA), tetrahydrocannabinol (THC), sugars and carbohydrates, lipids, plant waxes, impurities and other cannabinoids to an activation zone and therein subjected to a carboxylation reaction at a decarboxylation temperature of about 90 to about 120° C. and a decarboxylation pressure of about −0.6 atm to 0.74 atm for a decarboxylation reaction time of about 5 to about 8 hours, or sufficient time for the decarboxylation reaction to occur and proceed to completion, said decarboxylation reaction time being sufficient to fully decarboxylate essentially all of the cannabidiolic acid (CBDA) and tetrahydrocannabinolic acid (THCA) to provide a decarboxylated cannabinoid oil comprising cannabidiol (CBD), tetrahydrocannabinol (THC), lipids, plant waxes, and other cannabinoids, and being essentially free of cannabidiolic acid (CBDA) and tetrahydrocannabinolic acid (THCA), and water washing the decarboxylated cannabinoid oil to remove at least a portion of the impurities to provide a washed decarboxylated cannabinoid oil;

e) admixing the washed decarboxylated cannabinoid oil with a dewaxing solvent having a dewaxing solvent volume ratio of 80 volume units of ethanol to 20 volume units water to provide a dewaxing feed stream and passing the dewaxing feed stream to a dewaxing zone containing a dewaxing column at a dewaxing column pressure of about 2.72 atm to about 4.08 atm (40-60 psi) and room temperature (20-25° C.), said dewaxing column containing a hydrophobic activated carbon adsorbent which is essentially free of hydroxyl groups, and having an average particle diameter of between 177 and 250 microns, and an iodine number of above 900 mg/g to remove at least a portion of the lipids and plant waxes and to provide a dewaxed cannabinoid oil stream comprising cannabidiol (CBD), tetrahydrocannabinol (THC), sugars and carbohydrates, color bodies, and other cannabinoids;

f) passing the dewaxed cannabinoid oil stream and a mobile phase desorbent stream consisting of a mixture of food grade ethanol and water to a reversed phase simulated moving bed zone comprising a plurality of adsorbent beds containing a modified hydrophobic adsorbent comprising a styrene-divinylbenzene (DVB) resin having 4 to 8 percent crosslinking or a poly (methyl methacrylate) (PMMA) resin, said modified hydrophobic adsorbent having an average particle diameter of between 25 and 300 microns, an average bulk density (gm/mL) of from 0.4 to 0.6, a surface area (m2/g) of from 450 to 550, and a pore volume of from 0.70-0.90 (mL/g) to provide a primary raffinate stream comprising cannabidiol (CBD), mobile phase desorbent, sugars and carbohydrates, color bodies, and other cannabinoids and being essentially free of tetrahydrocannabinol (THC), an extract stream comprising mobile phase desorbent, cannabidiol (CBD), and tetrahydrocannabinol (THC), and a secondary raffinate stream comprising mobile phase desorbent, cannabidiol (CBD) which is admixed with the mobile phase desorbent and returned to the reversed phase simulated moving bed zone;

g) passing the primary raffinate to a second evaporation zone to remove mobile phase desorbent to provide a second recovered solvent stream comprising the mobile phase desorbent and to provide the high purity cannabinoid oil stream having an average cannabidiol purity of greater than 80 wt % and being essentially free of tetrahydrocannabinol (THC);

h) passing at least a portion of the high purity cannabinoid oil stream to a polishing zone and therein admixing the high purity cannabinoid oil stream with a non-polar solvent stream comprising hexane and therein allowing the admixture to settle to form a precipitate comprising sugars and carbohydrates and a supernatant non-polar solution comprising cannabidiol (CBD), color bodies, and other cannabinoids;

i) passing a portion of the supernatant non-polar solution to a second filtration zone to remove the precipitate and to provide a filtered supernatant non-polar solution;

j) passing the filtered supernatant non-polar solution to a third evaporation zone to remove at least a portion of the non-polar solvent to provide an evaporated cannabinoid oil stream and a recovered non-polar solvent stream, and returning at least a portion of the recovered non-polar solvent stream to the polishing zone to be admixed with the non-polar solvent;

k) passing the evaporated cannabinoid oil stream to a wash zone and alternately washing the evaporated cannabinoid oil stream first with an ethanol wash stream comprising pure ethanol in a washing ratio of 1:3 liters of ethanol to kilograms of evaporated cannabinoid oil, and second with a fourth water wash stream in a water wash ratio of 1:3 liters of water to kilograms of evaporated cannabinoid oil, and wherein following each step, washed cannabinoid oil is evaporated to dryness to provide a phytocannabinoid rich oil which is essentially free of tetrahydrocannabinol (THC) and comprising greater than 80 wt-% cannabinoid (CBD);

l) passing a portion of the supernatant non-polar solution to a isolate chromatography zone comprising a first isolate chromatography column and a second isolate chromatography column being in serial fluid communication and wherein the first isolate chromatography column contains a modified hydrophilic adsorbent comprising a spherical polar silica adsorbent having a high level of silenol groups, an average particle diameter of between 60 and 200 microns, a surface area of between 450 to 550 m2/g a pore volume of between 0.7 and 0.85 mL/g and a pore size of between 0.005 and 0.0075 microns, wherein the second isolate chromatography column contains an activated alumina adsorbent having an average particle diameter of between 50 to 200 microns, an average bulk density of 0.85 g/ml, a surface area of between 140 and 170 m2/g, and an average pore diameter of greater than 0.006 microns to provide an isolate elute stream comprising cannabidiol (CBD), non-polar solvent and other cannabinoids;

m) passing the isolate elute stream to a crystallization zone, wherein the isolate elute stream is subjected to a freezer temperature of equal to or less than about −20° C. for a freezer period of about 24 to about 72 hours to permit primary high purity cannabidiol crystals, containing from about 96 to about 98 wt-% cannabidiol to form, harvesting the primary high purity cannabidiol (CBD) crystals and admixing the primary high purity cannabidiol crystals with hexane to provide the crystal isolate solution comprising 20-30% by weight cannabidiol CBD oils, and retaining the crystal isolate solution at room temperature for a period of 24-72 hours to permit secondary high purity CBD crystals to form and harvesting the secondary high purity CBD crystals;

n) passing the secondary high purity CBD crystals to a rotary evaporation zone wherein the secondary high purity crystals are heated until molten to evaporate any residual non-polar and washed with a third water wash stream at least three times in the rotary evaporation, wherein at the completion of each wash step the secondary high purity crystals are dried to complete dryness to provide a solid CBD aggregate which is essentially free of tetrahydrocannabinol (THC) and has a cannabidiol purity of greater than 99 wt-%; and, o) withdrawing at least one high purity cannabidiol product being essentially free of tetrahydrocannabinol (THC) a stream selected from the group consisting of the high purity cannabinoid oil stream, the phytocannabinoid rich oil, the solid CBD aggregate and mixtures thereof.

2. The process of claim 1, further comprising passing solid CBD aggregate to a granulator to provide a powdered high purity CBD product which has a cannabidiol purity of greater than 99 wt-% and is essentially free of tetrahydrocannabinol.

3. The process of claim 1, wherein the primary raffinate stream has a solids concentration of about 5 to about 7 grams per liter.

4. The process of claim 1, wherein the modified hydrophobic adsorbent comprises a styrene-divinylbenzene (DVB) resin having 4 to 8 percent crosslinking.

5. The process of claim 1, wherein the mobile phase desorbent stream consists of a mixture of food grade ethanol and water having an ethanol to water ratio of 80 parts to 20 parts ethanol volume/volume.

6. The process of claim 1, wherein the reverse phase simulated moving bed zone comprises is a 2-3-2-1 arrangement, wherein 2 adsorbent beds are operated in a desorption zone, 3 adsorbent beds are operated in a rectification zone, 2 adsorbent beds are operated in an adsorption zone, and 1 adsorbent bed is operated in a concentration zone.

7. A process for the purification of cannabidiol (CBD) in a crude *cannabis* extract stream to provide at least one high purity cannabidiol product being essentially free of tetrahydrocannabinol, said process comprising:

a) passing the crude *cannabis* extract stream comprising debris and small particles, cannabidiol, tetrahydrocannabinol, cannabidiolic acid, tetrahydrocannabinolic acid, other cannabinols, chlorophylls, color bodies, sugars and carbohydrates, lipids, plant waxes, impurities, and ethanol to a first filtration zone comprising a series of successive filters of decreasing pore size, starting at a pore size of 100 microns and reducing to about 10 microns in 3 or more stages to remove debris and small particles in a progressive filtration step to provide a filtered crude cannabinoid stream;

b) passing the filtered crude cannabinoid stream comprising cannabidiol, tetrahydrocannabinol, cannabidiolic acid, tetrahydrocannabinolic acid, other cannabinols, chlorophylls, color bodies, sugars and carbohydrates, lipids, plant waxes, impurities, and ethanol to a decolorization zone comprising a 10 µm filter and a decolorization chromatographic column containing a modified activated carbon adsorbent which was heat treated to provide a highly hydrophobic adsorbent which is essentially free of hydroxyl groups, has an average particle diameter of between 177 and 250 microns, and an iodine number of above 900 mg/g and operated at a decolorization pressure of 2.72 atm to about 4.08 atm (40-60 psig) and a decolorization temperature ranging from 20-25° C. to remove at least a portion of color bodies and essentially all of the chlorophyll to provide a decolorized extract stream;

c) passing the decolorized extract stream to a first evaporation zone operated at a first vacuum pressure of −0.60 to about −0.74 atm (−18 to −22 in Hg) and a temperature of about 90 to about 110° C. to remove at least a portion of the ethanol to provide an evaporated extract stream which is essentially free of ethanol;

d) passing the evaporated extract stream comprising cannabidiol (CBD), cannabidiolic acid (CBDA), tetrahydrocannabinolic acid (THCA), tetrahydrocannabinol (THC), sugars and carbohydrates, lipids, plant waxes, impurities and other cannabinoids to an activation zone and therein subjected to a carboxylation reaction at a decarboxylation temperature of about 90 to about 120° C. and a decarboxylation pressure of about −0.6 atm to 0.74 atm for a decarboxylation reaction time of about 5 to about 8 hours, or sufficient time for the decarboxylation reaction to occur and proceed to completion, said decarboxylation reaction time being sufficient to fully decarboxylate essentially all of the cannabidiolic acid (CBDA) and tetrahydrocannabinolic acid (THCA) to provide a decarboxylated cannabinoid oil comprising cannabidiol (CBD), tetrahydrocannabinol (THC), lipids, plant waxes, and other cannabinoids, and being essentially free of cannabidiolic acid (CBDA) and tetrahydrocannabinolic acid (THCA), and water washing the decarboxylated cannabinoid oil to remove at least a portion of the impurities to provide a washed decarboxylated cannabinoid oil;

e) admixing the washed decarboxylated cannabinoid oil with a dewaxing solvent having a dewaxing solvent volume ratio of 80 volume units of ethanol to 20 volume units water to provide a dewaxing feed stream and passing the dewaxing feed stream to a dewaxing zone containing a dewaxing column at a dewaxing column pressure of about 2.72 atm to about 4.08 atm (40-60 psi) and room temperature (20-25° C.), said dewaxing column containing a hydrophobic activated carbon adsorbent which is essentially free of hydroxyl groups, and having an average particle diameter of between 177 and 250 microns, and an iodine number of above 900 mg/g to remove at least a portion of the lipids and plant waxes and to provide a dewaxed cannabinoid oil stream comprising cannabidiol (CBD), tetrahydrocannabinol (THC), sugars and carbohydrates, color bodies, and other cannabinoids;

f) passing the dewaxed cannabinoid oil stream and a mobile phase desorbent stream consisting of a mixture of food grade ethanol and water to a reversed phase simulated moving bed zone comprising a plurality of adsorbent beds containing a modified hydrophobic adsorbent comprising a styrene-divinylbenzene (DVB) resin having 4 to 8 percent crosslinking or a poly (methyl methacrylate) (PMMA) resin, said modified hydrophobic adsorbent having an average particle diameter of between 25 and 300 microns, an average bulk density (gm/mL) of from 0.4 to 0.6, a surface area (m2/g) of from 450 to 550, and a pore volume of from 0.70-0.90 (mL/g) to provide a primary raffinate stream comprising cannabidiol (CBD), mobile phase desorbent, sugars and carbohydrates, color bodies, and other cannabinoids and being essentially free of tetrahydrocannabinol (THC), an extract stream comprising mobile phase desorbent, cannabidiol (CBD), and tetrahydrocannabinol (THC), and a secondary raffinate stream comprising mobile phase desorbent, cannabidiol (CBD) which is admixed with the mobile phase desorbent and returned to the reversed phase simulated moving bed zone;
g) passing the primary raffinate to a second evaporation zone to remove mobile phase desorbent to provide a second recovered solvent stream comprising the mobile phase desorbent and to provide a high purity cannabinoid oil stream having an average cannabidiol purity of greater than 80 wt % and being essentially free of tetrahydrocannabinol (THC); and,
h) withdrawing the high purity cannabinoid oil stream as the at least one high purity cannabidiol product having an average cannabidiol purity of greater than 80 wt %.

8. The process of claim 7 further comprising:
a) passing at least a portion of the high purity cannabinoid oil stream to a polishing zone and therein admixing the high purity cannabinoid oil stream with a non-polar solvent stream comprising hexane and therein allowing the admixture to settle to form a precipitate comprising sugars and carbohydrates and a supernatant non-polar solution comprising cannabidiol (CBD), color bodies, and other cannabinoids;
b) passing a portion of the supernatant non-polar solution to a second filtration zone to remove the precipitate and to provide a filtered supernatant non-polar solution;
c) passing the filtered supernatant non-polar solution to a third evaporation zone to remove at least a portion of the non-polar solvent to provide an evaporated cannabinoid oil stream and a recovered non-polar solvent stream, and returning at least a portion of the recovered non-polar solvent stream to the polishing zone to be admixed with the non-polar solvent;
d) passing the evaporated cannabinoid oil stream to a wash zone and alternately washing the evaporated cannabinoid oil stream first with an ethanol wash stream comprising pure ethanol in a washing ratio of 1:3 liters of ethanol to kilograms of evaporated cannabinoid oil, and second with a fourth water wash stream in a water wash ratio of 1:3 liters of water to kilograms of evaporated cannabinoid oil, and wherein following each step, washed cannabinoid oil is evaporated to dryness to provide a phytocannabinoid rich oil which is essentially free of tetrahydrocannabinol (THC) and comprising greater than 80 wt-% cannabinoid (CBD); and,
e) withdrawing the phytocannabinoid rich oil as the high purity cannabidiol product having an average cannabidiol purity of greater than 80 wt %.

9. The process of claim 7 further comprising:
a) passing at least a portion of the high purity cannabinoid oil stream to a polishing zone and therein admixing the high purity cannabinoid oil stream with a non-polar solvent stream comprising hexane and therein allowing the admixture to settle to form a precipitate comprising sugars and carbohydrates and a supernatant non-polar solution comprising cannabidiol (CBD), color bodies, and other cannabinoids;
b) passing a portion of the supernatant non-polar solution to a isolate chromatography zone comprising a first isolate chromatography column and a second isolate chromatography column being in serial fluid communication and wherein the first isolate chromatography column contains a modified hydrophilic adsorbent comprising a spherical polar silica adsorbent having a high level of silenol groups, an average particle diameter of between 60 and 200 microns, a surface area of between 450 to 550 m2/g a pore volume of between 0.7 and 0.85 mL/g and a pore size of between 0.005 and 0.0075 microns, wherein the second isolate chromatography column contains an activated alumina adsorbent having an average particle diameter of between 50 to 200 microns, an average bulk density of 0.85 g/ml, a surface area of between 140 and 170 m2/g, and an average pore diameter of greater than 0.006 microns to provide an isolate elute stream comprising cannabidiol (CBD), non-polar solvent and other cannabinoids;
c) passing the isolate elute stream to a crystallization zone, wherein the isolate elute stream is subjected to a freezer temperature of equal to or less than about −20° C. for a freezer period of about 24 to about 72 hours to permit primary high purity cannabidiol crystals, containing from about 96 to about 98 wt-% cannabidiol to form, harvesting the primary high purity cannabidiol (CBD) crystals and admixing the primary high purity cannabidiol crystals with hexane to provide the crystal isolate solution comprising 20-30% by weight cannabidiol CBD oils, and retaining the crystal isolate solution at room temperature for a period of 24-72 hours to permit secondary high purity CBD crystals to form and harvesting the secondary high purity CBD crystals;
d) passing the secondary high purity CBD crystals to a rotary evaporation zone wherein the secondary high purity crystals are heated until molten to evaporate any residual non-polar and washed with a third water wash stream at least three times in the rotary evaporation, wherein at the completion of each wash step the secondary high purity crystals are dried to complete dryness to provide a solid CBD aggregate which is essentially free of tetrahydrocannabinol (THC) and has a cannabidiol purity of greater than 99 wt-%; and,
e) withdrawing the solid CBD aggregate as the high purity cannabidiol product having an average cannabidiol purity of greater than 99 wt-%.

10. The process of claim 1, further comprising the following leaf extraction steps prior to step a):
i) combining dry hemp leaves with a first portion of food grade ethanol to provide a first leaf/solvent mixture and agitating the first leaf/solvent mixture;
ii) soaking the first leaf/solvent mixture for an effective soaking time to form a first ethanol layer;
iii) decanting the first ethanol layer to provide a first decant stream and a first portion of wet leaves;
iv) combining a second portion of food grade ethanol with the first portion of wet leaves to provide a second leaf/solvent mixture and agitating the second leaf/solvent mixture and decanting a second ethanol layer to provide a second decant stream and residual leaves; and,
v) pressing the residual leaves to provide a third decant stream and combining the first decant stream, the second decant stream and the third decant streams to provide the crude *cannabis* extract stream.

11. The process of claim 10 wherein the effective soaking time comprises about 8 to 12 hours.

12. The process of claim 9, further comprising passing a portion of the supernatant non-polar solution to a second filtration zone to remove the precipitate and to provide a filtered supernatant non-polar solution and passing the filtered supernatant non-polar solution to the isolate chromatography zone.

* * * * *